United States Patent [19]

Ellingboe et al.

[11] Patent Number: 5,149,700
[45] Date of Patent: Sep. 22, 1992

[54] SUBSTITUTED ARYLSULFONAMIDES AND BENZAMIDES

[75] Inventors: John W. Ellingboe; Jehan F. Bagli, both of Princeton, N.J.; Michael W. Winkley, St. Albans, Vt.

[73] Assignee: American Home Products Corporation, New York, N.Y.

[21] Appl. No.: 785,136

[22] Filed: Oct. 30, 1991

Related U.S. Application Data

[63] Continuation of Ser. No. 530,684, May 30, 1990, abandoned.

[51] Int. Cl.⁵ .................. A61K 31/505; A61K 31/47; C07D 329/02; C07D 401/00
[52] U.S. Cl. ..................................... 514/275; 514/313; 514/388; 514/393; 514/395; 544/323; 544/332; 546/163; 546/169; 548/305; 548/306; 548/324; 548/325
[58] Field of Search ............... 544/323, 332, 163, 169; 548/305, 306, 324, 325; 514/275, 313, 388, 395, 393

[56] References Cited

U.S. PATENT DOCUMENTS

| 4,159,331 | 6/1979 | McCall | 514/242 |
| 4,459,296 | 7/1984 | Ancher et al. | 514/254 |
| 4,544,654 | 10/1985 | Davey et al. | 514/210 |
| 4,721,809 | 1/1988 | Buzby, Jr. | 564/82 |
| 4,882,323 | 11/1989 | Winkley et al. | 514/183 |

FOREIGN PATENT DOCUMENTS 2091255  7/1982  United Kingdom .

OTHER PUBLICATIONS

Sol S. Klioze et al., J. Med. Chem. 1980, 23(6) 677-679.
Chem. Abstracts 93: 46595w, 1980.

Primary Examiner—Mukund J. Shah
Assistant Examiner—Matthew V. Grumbling
Attorney, Agent, or Firm—Walter Patton

[57] ABSTRACT

This invention relates to substituted arylsulfonamides and benzamides possessing aniarrhythmic activity, to pharmaceutical compositions and to methods for production thereof.

21 Claims, No Drawings

SUBSTITUTED ARYLSULFONAMIDES AND BENZAMIDES

This is a continuation of application Ser. No. 07/530,684 filed May 30, 1990, now abandoned.

BACKGROUND OF THE INVENTION

Class III antiarrhythmic agents may be categorized as having the ability to markedly prolong cardiac action potential duration without producing significant changes in maximal upstroke velocity. Unlike Class I antiarrhythmic agents, a pure Class III agent displays no effect on cardiac sodium channels. The electrophysiologic properties of a compound defining a Class III activity profile are observed in vivo as negligible effects on atrial, ventricular and H-V conduction times while producing a marked increase (greater than 20 percent) in both the atrial and ventricular refractory period. In contrast, Class I agents will demonstrate a marked slowing of ventricular conduction velocity, often without significant changes in the refractory period. Recent reviews of these agents are: Bexton et al.; Pharmac. Ther. 17, 315-55 (1982); Vaughan-Williams, J. Clin. Pharmacol. 24, 129-47 (1984); Steinberg et al., Ann. Rep. Med. Chem. 21, 95-108 (1986) and Colatsky and Follmer, Drug Development Research 19; 129-140 (1990).

Buzby et al. recently disclosed 4-methylsulfonamido-N-[2-[(1-methylethyl)amino]ethyl]benzenesulfonamide as a potential Class III antiarrhythmic agent in U.S. Pat. No. 4,721,809, Jan. 26, 1988.

Davey et al. disclosed N-[2-(diethylamino)ethyl-4-[(methylsulfonyl)amino]benzamide as a potential Class III antiarrhythmic agent in U.S. Pat. No. 4,544,654, Oct. 1, 1985.

Winkley et al. disclosed N-[4-[(2,3,5,6-tetrahydro-[1,3,6]triazocino[1,2-a]benzimidazol-4-(1H)-yl)sulfonyl]phenyl]methanesulfonamide as a potential Class III antiarrhythmic agent in U.S. Pat. No. 4,882,323, Nov. 21, 1989.

The compounds of the present invention differ from those disclosed by Buzby et al. and Davey et al. by the presence of a nitrogen containing heterocycle ($R^4$ in general formula (I) below). They differ from the compounds disclosed by Winkley et al. in that they lack a triazocino group.

DESCRIPTION OF THE INVENTION

This invention relates to substituted arylsulfonamides and benzamides of the general formula (I):

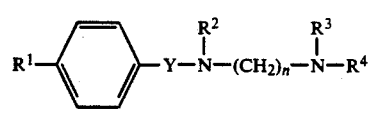

wherein $R^1$ is H, $NHSO_2CH_3$, $NO_2$, or 1-imidazolyl; Y is $SO_2$ or $C(O)$; n is 2 or 3; $R^2$ and $R^3$ are lower alkyl containing 1 to 6 carbon atoms or, when n is 2, $R^2$ and $R^3$ are joined to form piperazine; $R^4$ is selected from the group consisting of:

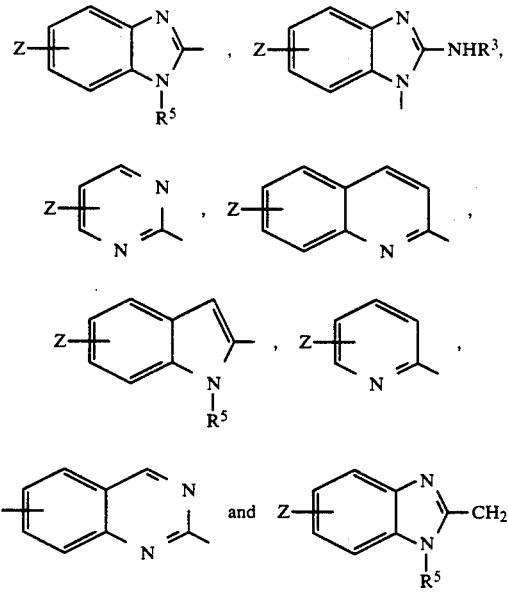

wherein $R^3$ and $R^5$ are lower alkyl containing 1 to 6 carbon atoms and Z is H or $NHSO_2CH_3$; or $R^3$ and $R^4$ are joined to form

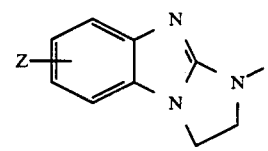

wherein Z is H or $NHSO_2CH_3$ and the pharmaceutically acceptable salts thereof.

A preferred aspect of the present invention is the compounds of formula (I) wherein $R^1$ is H or $NHSO_2CH_3$; Y is $SO_2$ or $C(O)$; n is 2 or 3; $R^2$ and $R^3$ are lower alkyl containing 1 to 6 carbon atoms or, when n is 2, $R^2$ and $R^3$ are joined to form piperazine; $R^4$ is selected from the group consisting of:

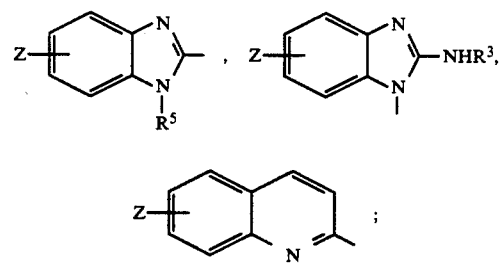

wherein $R^3$ and $R^5$ are lower alkyl containing 1 to 6 carbon atoms and Z is H or $NHSO_2CH_3$; or $R^3$ and $R^4$ are joined to form

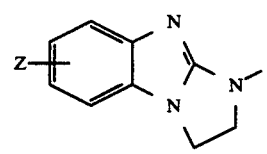

wherein Z is H or NHSO₂CH₃ and the pharmaceutically accepted salts thereof.

A further preferred aspect of the present invention are the compounds:

N-methyl-N-[2-[methyl(1-methyl-1H-benzimidazol-2-yl)amino]ethyl]-4-[(methylsulfonyl)amino]benzenesulfonamide;

4-[(methylsulfonyl)amino]-N-[2-(2-pyrimidinylamino)ethyl]benzenesulfonamide;

N-methyl-N-[2-[methyl(1-methyl-1H-benzimidazol-2-yl)amino]ethyl]-4-[(methylsulfonyl)amino]benzamide;

4-[(methylsulfonyl)amino]-N-[2-[(quinolin-2-yl)amino]ethyl]benzenesulfonamide;

N-methyl-N-[2-[methyl(1-ethyl-1H-benzimidazol-2-yl)amino]ethyl]-4-[(methylsulfonyl)amino]benzenesulfonamide;

N-methyl-N-[2-[methyl[(1-methyl-1-benzimidazol-2-yl)methyl]amino]ethyl]-4-[(methylsulfonyl)amino]benzamide;

N-methyl-N-[2-[methyl[(1-methyl-1H-benzimidazol-2-yl)methyl]amino]ethyl]-4-[(methylsulfonyl)amino]benzenesulfonamide;

N-methyl-N-[2-[methyl(quinolin-2-yl)amino]ethyl]-4-[(methylsulfonyl)amino]benzenesulfonamide;

N-methyl-N-[2-[methyl[5-[(methylsulfonyl)amino]-1H-benzimidazol-2-yl]amino]ethyl]benzamide;

N-methyl-N-[2-(2,3-dihydro-1H-imidazo[1,2-a]benzimidazol-1-yl)ethyl]-4-[(methylsulfonyl)amino]benzenesulfonamide;

N-methyl-N-[2-[methyl(quinolin-2-yl)amino]ethyl]-4-[(methylsulfonyl)amino]benzamide;

N-[2-[(1H-benzimidazol-2-ylmethyl)methylamino]ethyl]-N-methyl-4-[(methylsulfonyl)amino]benzenesulfonamide;

N-methyl-N-[3-[methyl(1-methyl-1H-benzimidazol-2-yl)amino]propyl]-4-[(methylsulfonyl)amino]benzenesulfonamide;

N-methyl-N-[2-[methyl(1H-benzimidazol-2-yl)amino]ethyl]-4-[(methylsulfonyl)amino]benzenesulfonamide;

N-[4-(1-methyl-1H-benzimidazol-2-yl)-1-piperazinyl]-4-[(methylsulfonyl)amino]benzamide;

N-[4-[[4-(1-methyl-1H-benzimidazol-2-yl)-1-piperazinyl]sulfonyl]phenyl]methanesulfonamide;

N-methyl-N-[2-(2-methylamino)-1H-benzimidazol-1-yl)ethyl]-4-[(methylsulfonyl)amino]benzenesulfonamide;

N-[2-[(1-methyl-1H-benzimidazol-2-yl)amino]ethyl]-4-[(methylsulfonyl)amino]benzenesulfonamide;

N-methyl-N-[2-[(1-methyl-1H-benzimidazol-2-yl)amino]ethyl]-4-[(methylsulfonyl)amino]benzenesulfonamide and the pharmaceutically acceptable salts thereof.

It is to be understood that the definition of the compounds of formula (I) encompass all possible stereoisomers and mixtures thereof which possess the activity discussed below. In particular, it encompasses racemic modifications and any optical isomers which possess the indicated activity.

The pharmaceutically acceptable salts of the antiarrhythmic agents of this invention are prepared directly by neutralization of the free base. These physiologically acceptable salts may be formed with organic or inorganic acids, such as hydrochloric, hydrobromic, phosphoric, sulfuric, sulfamic, nitric, methylsulfonic, acetic, maleic, succinic, fumaric, tartaric, citric, salicylic, lactic, napthalenesulfonic acid and the like.

PROCESS

The compounds of the present invention are prepared according to the general sequences outlined in Schemes I and II below:

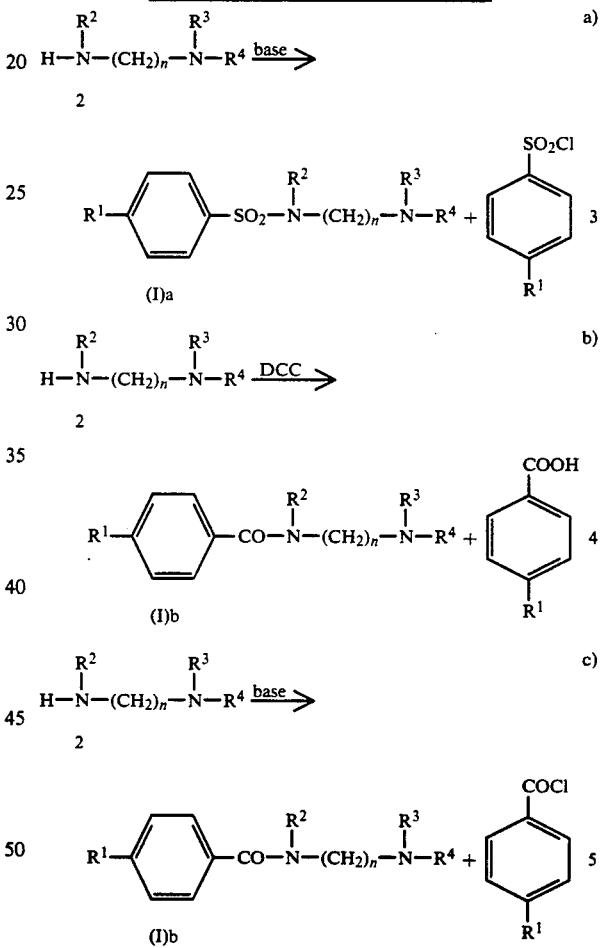

wherein $R^1$, $R^2$, $R^3$, $R^4$ and n are as defined above. (I)a designates those compounds of formula (I) wherein Y is $SO_2$. (I)b designates those compounds of formula (I) wherein Y is C(O).

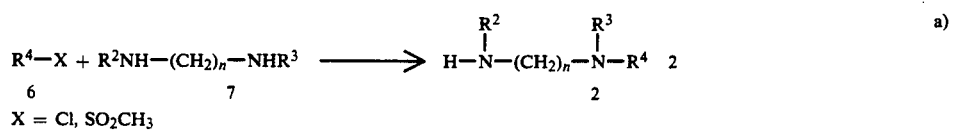

-continued
Scheme II: Preparation of 2

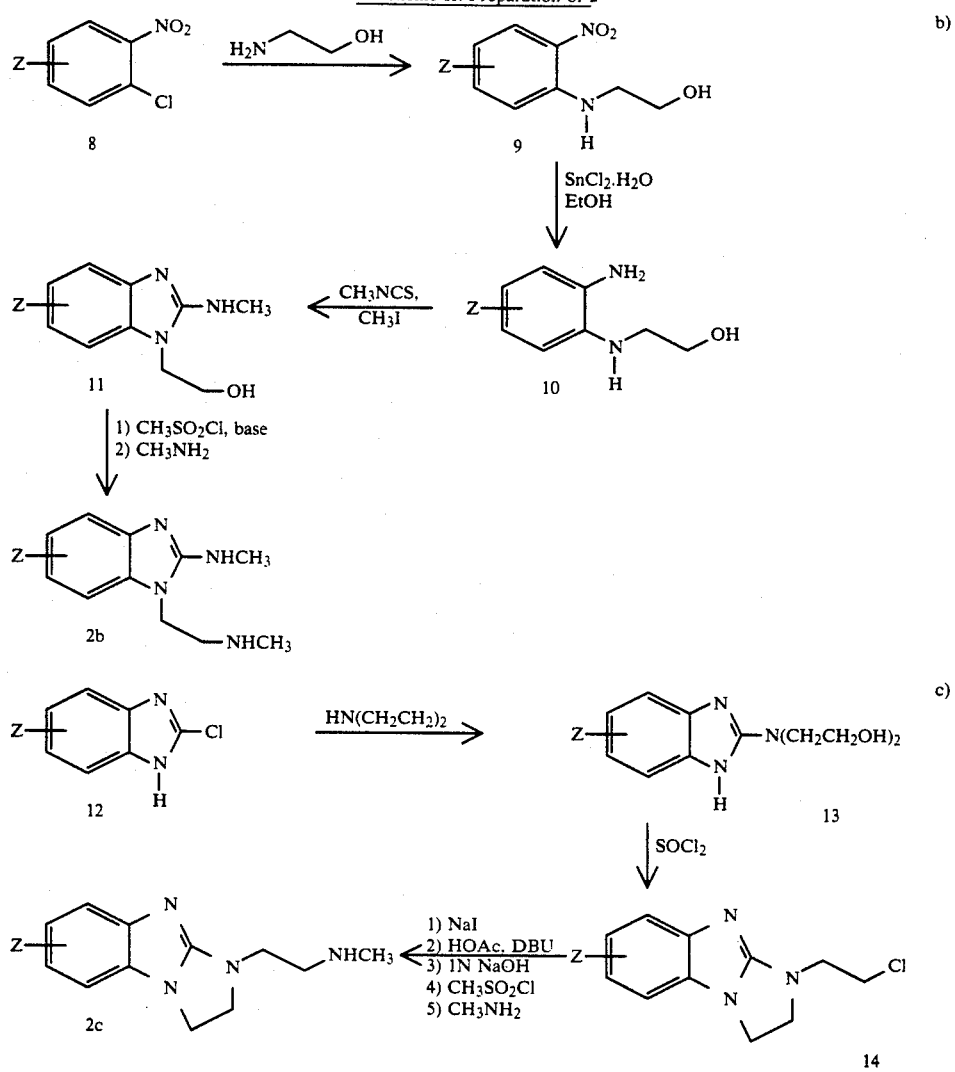

wherein $R^2$, $R^3$, $R^4$ and Z are as defined above.

PROCESS

All of the benzenesulfonamides (I)a (Scheme Ia) are prepared from the amines 2 by treatment with an arylsulfonyl chloride 3 in the presence of an amine base such as triethylamine or pyridine, in an inert organic solvent such as dichloromethane, chloroform, or tetrahydrofuran at ambient temperatures.

The benzamides (I)b (Scheme Ib) are prepared from the amines 2 by treatment with a benzoic acid 4 in the presence of amide coupling reagents such as dicyclohexylcarbodiimide (DCC) and 1-hydroxybenztriazole (HOBT), in an inert organic solvent or combination of solvents such as tetrahydrofuran and dimethylformamide at ambient temperatures.

The benzamides (I)b (Scheme Ic) can also be prepared by treatment of the amines 2 with a benzoyl chloride 5 in the presence of an amine base such as triethylamine or pyridine, in an inert organic solvent such as dichloromethane, chloroform, or tetrahydrofuran, at low (−23° C. to 5° C.) to ambient temperatures.

The intermediate amines 2 (Scheme IIa) are prepared from a substituted heterocycle 6 by treatment with a diamine 7 in the presence of an amine base such as triethylamine or an inorganic base such as sodium or potassium carbonate with or without an alcoholic solvent such as ethanol, 1-butanol, or 3-methyl-1-butanol, at temperatures ranging from ambient to reflux.

The intermediate amine 2b (Scheme IIb) is prepared from 2-chloronitrobenzene 8 by treatment with ethanolamine in an alcoholic solvent such as ethanol, 1-butanol, or 3-methyl-1-butanol at temperatures from ambient to reflux; reduction of the nitro group in compound 9 with tin(II) chloride in ethanol at temperatures from ambient to reflux; conversion of the diaminobenzene 10 to the benzimidazole 11 by treatment with methyl isocyanate and iodomethane in an alcoholic solvent such as methanol, ethanol, or 1-butanol at temperatures ranging from ambient to reflux; and conversion of the hydroxy group in 11 to a methylamino group by formation of a mesylate with methanesulfonyl chloride, in the presence of an amine base such as triethylamine or pyridine, in an inert organic solvent such as dichloromethane, chloroform, or tetrahydrofuran, at low (−23° C. to 5° C.) to ambient temperatures, and subsequent treatment with methylamine in water or an alcoholic solvent at ambient temperatures.

The intermediate amine 2c is prepared from 2-chlorobenzimidazole 12 by treatment with diethanolamine in an alcoholic solvent such as 1-butanol or 3-methyl-1-butanol at temperatures ranging from ambient to reflux to yield the substituted benzimidazole 13; cyclization to the imidazo[1,2-a]benzimidazole 14 by treatment with thionyl chloride and dimethylformamide at temperatures ranging from ambient to reflux; and conversion of the chloro group to a methylamino group by the following sequence: replacement of the chloride by an iodide by treatment with sodium iodide in a ketone solvent such as acetone or 2-butanone at temperatures ranging from ambient to reflux, and treatment with methylamine in water or an alcoholic solvent at ambient temperature.

PHARMACOLOGICAL METHODS

Cardiac Electrophysiology

The compounds of this invention display a Class III antiarrhythmic profile. The class III antiarrhythmic activity was established in vitro and in vivo in accordance with the following standard test procedures:

In Vitro

Bundles of free-running Purkinje fibers with attached myocardium obtained from either ventricle of adult dog heart were pinned without stretching to the bottom of a 10 mL tissue chamber and continuously superfused with oxygenated Tyrode's solution at a flow rate of 5 mL/min. The composition of the Tyrode's solution was (mM): NaCl, 138; KCl, 4; $CaCl_2$, 2; $MgCl_2$, 0.5; $NaHCO_3$, 24; dextrose, 5.5. The solution was aerated with 95% $O_2$/5% $CO_2$ at 37° C. The bath temperature was maintained at 37°±0.5° C. by circulating the pre-warmed superfusate through a thermostatically controlled water bath immediately prior to entering the tissue chamber.

The preparations were stimulated through bipolar Teflon-coated silver wires, bared at the tips, placed on the endocardial surface of the attached myocardium, using a digital stimulator set to deliver constant current pulses 1.5 msec. in duration at cycle lengths of 300 or 1000 msec. Stimulus strength was set at approximately 2×diastolic threshold, and adjusted as required throughout the experiment. All preparations were allowed to equilibrate in the tissue chamber for at least 1 hour before measurements were begun. Subsequently, a minimum of 60 minutes were allowed for equilibration with each drug-containing superfusate before post-drug measurements were made. Impalements were made at 6 to 10 sites throughout the preparation before and after drug exposure. Offset potentials were rechecked after each impalement.

Glass microelectrodes filled with 3M KCl were coupled to high impedance negative capacitance electrometers and Ag/AgCl half-cells used as reference electrodes. The first derivative of the action potential upstroke ($V_{max}$) was obtained using an analog differentiator circuit, coupled to a peak-hold circuit that retained the recorded value of $V_{max}$ for 30 to 70 msec. Action potential and $V_{max}$ tracings were displayed on a storage oscilloscope, and photographed for later analysis. In addition, chart paper recordings of $V_{max}$ were obtained using the peak-hold device output.

Fresh stock solutions of drug were prepared for each experiment. Compounds were dissolved in distilled water at total concentrations of 1 to 10 mg/mL, and subsequently diluted to a final concentration of 3 to 10 μM in appropriate volumes of normal Tyrode's solution for evaluation.

Action potential (AP) parameters measured included: diastolic take-off potential (or activation voltage ($V_{act}$); AP overshoot ($V_{os}$); AP duration measured as the time taken to repolarize to −20 mV ($APD_{-20}$), −60 mV ($APD_{-60}$), and −80 mV ($APD_{-80}$); and maximal upstroke velocity ($V_{max}$). An increase in $APD_{-60}$ that occurred without a significant change in $V_{max}$ was taken, by definition, to indicate Class III antiarrhythmic activity "in vitro".

In Vivo

Mongrel dogs of both sexes weighing 12 to 18 kg were anesthetized with sodium pentobarbital (35 mg/kg i.v. supplemented with 5 mg/kg/h) and artificially ventilated with room air (minute volume: 200 mL/kg).

The heart was exposed by a right thoracotomy performed at the fifth intercostal space and suspended in a pericardial cradle. Epicardial electrodes for stimulation and recording were sutured to the free wall of the lower right atrium and near the base of the right ventricle. Each electrode set contained a linear array of electrodes consisting of 1 bipolar stimulating electrode and 2 bipolar recording electrodes embedded in a rigid acrylic matrix. The stimulating bipole was 7 mm from the proximal recording electrode, which in turn was 10 mm from the distal recording bipole. Each electrode array was oriented to be parallel to the epicardial fiber axis.

Arterial blood pressure and lead ECG were displayed on a chart recorder and monitored on an oscilloscope. Conduction times and refractory periods were measured during pacing at a cycle length of 300 msec. The dog heart was placed by a stimulator driving a constant current isolation unit. Electrical signals from the atrial and ventricular electrodes were displayed on a digital oscilloscope and recorded on an ink-jet recorder. The diastolic threshold was determined before and after each trial.

Refractory periods of the right atrium (AERP) and right ventricle (VERP) were determined by introducing an extrastimulus ($S_2$) every 8 paced beats ($S_1$). The extrastimulus was followed by a 4-second rest interval during which no pacing occurred. Both $S_1$ and $S_2$ were of identical intensity (twice threshold) and duration (2 msec). The $S_1$–$S_2$ interval was gradually decreased in 2 msec steps until the extrastimulus failed to induce a propagated response. This $S_1$–$S_2$ interval was considered to define the effective refractory period.

Atrial and ventricular conduction times (ACT and VCT) were measured as the time interval between the two electrograms recorded at the proximal and distal sites of the recording electrode array. The time of activation for electrograms with predominantly biphasic complexes was taken as the moment when the trace crossed the zero reference line, and for triphasic complexes, as the peak of the major deflection.

Animals received the test compound by i.v. injection. Drugs were administered cumulatively at the following dose levels: 1, 2.5, 5, 7.5, and 10 mg/kg. Each dose was administered over a 3 minute period. Electrophysiologic testing was performed 15 minutes following the end of dosing. Every 30 minutes the dog received the next incremental dose.

Vehicle-treated animals did not show any significant change of the electrophysiologic parameters. An increase in ERP that occurred without a significant decrease of CT was taken, by definition, to indicate "in vivo" Class III antiarrhythmic activity.

The results of the assays are set forth in the tables below.

TABLE 1

IN VITRO DATA[1]

| Example | BCL = 300 | | BCL = 1000 | | |
|---|---|---|---|---|---|
| | $APD_{-60}$ | $V_{max}$ | $APD_{-60}$ | $V_{max}$ | |
| 1 | 55* | −23* | 56 | 2 | (*BCL = 350) |
| | 29 | −8 | 96 | 23 | (0.3 uM) |
| 2 | 0 | 1 | 11 | 24 | |
| 3 | 13 | 1 | 12 | 2 | |
| 4 | 26 | 8 | 40 | −3 | |
| 5 | 28 | −7 | 36 | 10 | |
| 6 | 17 | −5 | 65 | −3 | |
| 7 | 18 | −7 | 58 | 15 | |
| 8 | — | — | — | — | |
| 9 | — | — | — | — | |
| 10 | — | — | — | — | |
| 11 | — | — | — | — | |
| 12 | 36 | 0 | 57 | −5 | |
| | 7 | 9 | 20 | 7 | (0.3 uM) |
| 13 | — | — | — | — | |
| 14 | — | — | — | — | |
| 15 | 36 | −5 | 94 | 7 | |
| | 6 | 14 | 17 | −1 | (0.3 uM) |
| 16 | −4 | −5 | −1 | −18 | |
| 17 | — | — | — | — | |
| 18 | (did not pace) | | 110 | −12 | |
| | 16 | −7 | 35 | −16 | (0.3 μM) |
| 19 | 16 | −5 | 36 | 7 | |
| 20 | — | — | — | — | |
| 21 | — | — | — | — | |
| 22 | — | — | — | — | |

[1]Purkinje fiber; percent change at 3 uM, unless otherwise noted
BCL: basic cycle length
$APD_{-60}$: action potential duration at −60 mV
$V_{max}$: action potential velocity, maximum

TABLE 2

IN VIVO DATA[1]

| Example | Dose | AERP | VERP | ACT | VCT | HR | BP | n |
|---|---|---|---|---|---|---|---|---|
| 1 | 1 | 29 | 20 | −6 | −1 | −14 | −15 | 2 |
| | 5 | 54 | 30 | −8 | −2 | −28 | −21 | 2 |
| | 5 (i.d.) | 49 | 24 | 13 | 9 | −15 | −7 | 2 |
| 6 | 1 | 18 | 10 | −1 | −1 | −6 | 5 | 2 |
| | 5 | 44 | 24 | −3 | −6 | −27 | −1 | 2 |
| 12 | 1 | 26 | 14 | −6 | 0 | −17 | −1 | 1 |
| | 5 | 47 | 27 | −9 | −8 | −32 | 0 | 1 |
| 15 | 1 | 33 | 19 | −10 | −8 | −17 | −10 | 2 |
| | 5 | 63 | 26 | −10 | −13 | −37 | −23 | 2 |
| 18 | 5 | 48 | 10 | 2 | −5 | −16 | −9 | 2 |
| | 10 | 60 | 12 | 4 | −6 | −19 | −18 | 2 |

[1]Anesthetized dog model; percent change
Dose: mg/Kg i.v., unless otherwise noted
AERP: effective refractory period for right atrium
VERP: effective refractory period for right ventricle
ACT: atrial conduction time
VCT: ventricular conduction time
HR: heart rate
BP: blood pressure
n: number of animals
i.d.: intra-duodenal administration Based upon the activity profile elicited by the compounds of this invention in the above-described standard scientifically recognized test models, the compounds are established as antiarrhythmic agents useful in the treatment of cardiac arrhythmias and conditions characterized by coronary artery vasospasms. For that purpose, the compounds may be administered orally or parenterally in suitable dosage forms compatible with the route of administration, whether oral, intraperitoneal, intramuscular, intravenous, internasal, buccal, etc. The effective dose range determined in the animal test models has been established at from about 1 to about 5 milligrams per kilogram host body weight (preferably from 2 to 10 mg/kg) i.v., and from about 2 to about 10 mg/kg (preferably 5 to 20 mg/kg) p.o., to be administered in single or plural doses as needed to relieve the arrhythmic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 50 milligrams to about 400 milligrams) of the active ingredient alone or in combination with adjuvants needed for conventional coating, tableting, solubilizing, flavoring or coloring. Parenteral administration with liquid dosage forms may be via sterile solutions or suspensions in aqueous or oleaginous medium. Isotonic aqueous vehicle for injection is preferred with or without stabilizers, preservatives and emulsifiers.

The following examples illustrate the preparation of a representative number of compounds of this invention.

EXAMPLE 1

N-Methyl-N-[2-[methyl(1-methyl-1H-benzimidazol-2-yl)amino]ethyl]-4-[(methylsulfonyl)amino]benzenesulfonamide Hydrochloride Step 1) Preparation of 2-Chlorobenzimidazole According to the procedure D. Harrison, et al., *J. Chem. Soc.*, 2930, 1963, a mixture of 2-hydroxybenzimidazole (40.0 g, 0.298 mol) and phosphoryl chloride (400 mL) was heated under reflux for 3 hours, cooled, and concentrated. The resulting slurry was poured onto ice and the solid (starting material) was removed by filtration. The filtrate was adjusted to pH 6 with 30% aqueous $NH_3$ and the resulting white precipitate was collected by filtration and dried to give 26.1 g (57%) of product m.p. 184°–186° C.

NMR (DMSO-$d_6$, 300 MHz): δ7.21 (m, 2H), 7.50 (m, 2H).

Step 2) Preparation of 2-Chloro-1-methylbenzimidazole

According to the procedure D. Harrison, et al., *J. Chem. Soc.*, 2930, 1963, to a cooled (5° C.), stirred solution of 2-chlorobenzimidazole (26.1 g, 0.171 mol) in DMF (125 mL) was added NaH (60% dispersion in mineral oil; 7.2 g, 0.180 mol) in several portions. After 30 minutes MeI (25.5 g, 0.180 mol) was added. The cooling bath was removed and stirring was continued for 30 minutes. The mixture was recooled, $H_2O$ (200 mL) was added, and the resulting precipitate was collected by filtration to give 20.2 g (71%) of product as an off-white solid m.p. 107°–109° C.

NMR (DMSO-$d_6$, 300 MHz): δ3.78 (s, 3H), 7.20–7.33 (m, 2H), 7.58 (m, 2H).

Step 3) Preparation of 2-[N-Methyl-N-[(2-methylamino)ethyl]amino]-1-methyl-1H-benzimidazole A solution of 2-chloro-1-methylbenzimidazole (5.00 g, 0.030 mol) in N,N'-dimethylethylenediamine (25 mL, 0.235 mol) was heated under reflux for 16 hours. The mixture was concentrated, dissolved in 10% aqueous HOAc (100 mL), and extracted with EtOAc. The aqueous phase was basified to pH 9 with solid KOH and extracted with EtOAc. The extracts were dried (MgSO₄) and concentrated to give a yellow oil 5.39 g (82%).

NMR (DMSO-d₆, 300 MHz): δ2.29 (s, 3H), 2.72 (t, J=6.7, 2H), 2.93 (s, 3H), 3.30 (t, J=6.7, 2H), 3.62 (s, 3H), 7.04 (m, 2H), 7.28 (m, 1H), 7.34 (m, 1H).

Step 4) Preparation of N-Methyl-N-[2-[methyl(1-methyl-1H-benzimidazol-2-yl)amino]ethyl]-4-[(methylsulfonyl)amino]benzenesulfonamide Hydrochloride To a stirred solution of 2-[N-methyl-N-[(2-methylamino)ethyl]amino]-1-methyl-1H-benzimidazole (5.4 g, 0.025 mol) and Et₃N (2.5 g, 0.025 mol) in CH₂Cl₂ (500 mL) was added 4-[(methylsulfonyl)amino]benzenesulfonyl chloride (6.7 g, 0.025 mol). After 18 hours (1 hour sufficient), the solution was washed with brine, saturated aqueous NaHCO₃, dried (MgSO₄) and concentrated to about 50 mL. The resulting white crystalline solid was collected by filtration 9.0 g of product m.p. 192°-193° C. The free base was suspended in MeOH (40 mL) and saturated methanolic HCl (100 mL) was added. All material went into solution, then a precipitate formed which was collected by filtration to give 7.6 g of product. This material was recrystallized from EtOH/H₂O (250 mL/10 mL) to give 6.1 g (50%) of colorless needles m.p. 210°-213° C.

NMR (DMSO-d₆, 400 MHz): δ2.67 (s, 3H), 3.12 (s, 3H), 3.29 (t, J=5.6, 2H), 3.36 (s, 3H), 3.83 (s,H), 3.87 (t, J=5.6, 2H), 7.35 (d, J=8.8, 2H), 7.50 (m, 2H), 7.64 (m, 2H), 7.71 (d, J=8.8, 2H), 10.51 (s, 1H), 13.90 (br s, 1H)

IR (KBr, cm⁻¹): 3400 (NH), 1625 (C=N)

MS (m/e): 452 (MH+)

Anal. Calcd. for C₁₉H₂₆ClN₅O₄S₂: C, 46.76; H, 5.37; N, 14.35%. Found: C, 46.70; H, 5.23; N, 14.34%.

EXAMPLE 2

4-[(Methylsulfonyl)amino]-N-[2-(2-pyrimidinylamino)ethyl]benzenesulfonamide

Step 1) Preparation of N-[2-[(Pyrimidin-1-yl)amino]ethylacetamide

A mixture of 2-chloropyrimidine (5.00 g, 0.0436 mol), sodium carbonate (4.63 g, 0.0436 mol), N-acetylethylenediamine (4.46 g, 0.0436 mol), and 3-methyl-1-butanol (100 mL) was heated under reflux for 19 hours. The mixture was filtered and the filtrate was concentrated. Trituration with ether gave an off-white solid 7.1 g (90%) m.p. 102°-103° C.

NMR (DMSO-d₆, 300 MHz): δ1.78 (s, 3H), 3.18 (m, 2H), 3.29 (m, 2H), 6.55 (dd, J=4.7, 4.7 1H); 7.09 (t, J=6.0, 1H), 7.95 (brs, 1H), 8.25 (d, J=4.7, 2H).

Step 2) Preparation of N-(Pyrimidin-1-yl)ethylenediamine

A solution of N-[2-[(pyrimidin-1-yl)amino]ethyl]acetamide (7.1 g, 0.039 mol) in 2.5N NaOH (47 mL, 0.118 mol) was heated under reflux for 22 hours. The mixture was cooled and the pH was adjusted to 8 with 2N HCl (38 mL). The mixture was concentrated, suspended in EtOH (100 mL) and filtered. The filtrate was concentrated to give an oily solid 4.7 g (87%).

NMR (DMSO-d₆, 300 MHz): δ2.67 (t, J=6.3, 2H), 3.25 (dt, J=6.0, 6.3, 2H), 6.53 (dd, J=4.7, 4.7, 1H), 7.10 (t, J=6.0, 1H), 8.24 (d, J=4.7, 2H).

Step 3) Preparation of 4-[(Methylsulfonyl)amino]-N-[2-(2-pyrimidinylamino)ethyl]benzenesulfonamide To a stirred solution of N-(pyrimidin-1-yl)ethylenediamine (4.70 g, 0.034 mol) and Et₃N (4.7 mL, 0.034 mol) in CH₂Cl₂ (900 mL) was added 4-[(methylsulfonyl)amino]benzenesulfonyl chloride (9.17 g, 0.034 mol). After 1.5 hours, the mixture was washed with brine, dried (MgSO₄), and concentrated. Trituration with hot CH₂Cl₂ (300 mL) gave 0.92 g (7%) of product as a white solid m.p. 150°-152° C.

NMR (DMSO-d₆, 400 MHz): δ2.87 (dt, J=6.0, 6.7, 2H), 3.10 (s, 3H), 3.27 (dt, J=6.0, 6.7, 2H), 6.55 (dd, J=4.8, 4.8, 1H), 7.05 (t, J=6.0, 1H), 7.30 (d, J=8.7, 2H), 7.61 (t, J=6.0, 1H), 7.71 (d, J=8.7, 2H), 8.22 (d, J=4.8, 2H), 10.34 (s, 1H)

IR (KBr, cm⁻¹): 3280 (NH), 1600 (C=N)

MS (m/e): 372 (M+)

Anal. Calcd. for C₁₃H₁₇N₅O₄S₂: C, 42.04; H, 4.61; N, 18.85%. Found: C, 41.84; H, 4.44; N, 18.50%.

EXAMPLE 3

N-[2-[(1H-Benzimidazol-2-ylmethyl)methylamino]ethyl]-N-methyl-4-[(methylsulfonyl)amino]benzensulfonamide Dihydrochloride Hydrate

Step 1) Preparation of 2-[[N-Methyl-N-[(2-methylamino)ethyl]amino]methyl]-1H-benzimidazole A mixture of 2-chloromethylbenzimidazole (4.00 g, 24 mmol), N,N'-dimethylethylenediamine (2.11 g, 24 mmol), potassium carbonate (3.32 g, 24 mmol) and ethanol (60 mL) was stirred at room temperature for 36 hours. The mixture was concentrated, taken up in H₂O and extracted with EtOAc. The combined extracts were dried and concentrated to give a brown oil. Purification by flash chromatography (eluent 5% MeOH/CH₂Cl₂) gave a colorless oil 2.42 g (40%).

NMR (DMSO-d₆, 300 MHz): δ3.05 (t, J=4.5 Hz, 2H), 3.18 (t, J=4.5 Hz, 2H), 3.4 (s, 3H), 4.37 (s, 2H), 4.67 (s, 3H), 7.38 (dd, J=8.7 Hz, 4.8 Hz, 1H), 7.40 (d, J=3.3 Hz, 1H), 7.71 (dd, J=6.4 Hz, 4.8 Hz, 1H), 7.74 (dd, J=6.4 Hz, 3.3 Hz, 1H), 9.15 (s, 1H).

Step 2) Preparation of N-[2-[(1H-Benzimidazol-2-ylmethyl)methylamino]ethyl]-N-methyl-4-[(methylsulfonyl)amino]benzenesulfonamide Dihydrochloride Hydrate To a stirred mixture of 2-[[N-methyl-N-[(2-methylamino)ethyl]amino]methyl]-1H-benzimidazole (2.42 g, 11.1 mmol), Et₃N (1.12 g, 11.1 mmol), and CHCl₃ (40 mL) was added 4-(methylsulfonyl)aminobenzenesulfonyl chloride (2.99 g, 11.1 mmol). After 2 hours, the mixture was concentrated, taken up in H₂O, and extracted with EtOAc. The extracts were washed with H₂O and brine, dried, and concentrated to give a yellow solid. Purification by flash chromatography (eluent 5% MeOH/CH₂Cl₂) gave an off-white solid. Saturated methanolic HCl (20 mL) was added. After several minutes, the solution was concentrated and triturated with hot EtOH. The material was recrystallized from EtOH/H₂O to give a white solid 2.12 g (42%) m.p. 194°-196° C.

NMR (DMSO-d₆, 400 MHz): δ2.70 (s, 3H), 2.86 (s, 3H), 3.14 (s, 3H), 3.37 (br s, 4H), 4.65 (s, 2H), 7.38 (dd, J=8.7 Hz, 4.0 Hz, 1H), 7.40 (d, J=3.3 Hz, 1H), 7.71

(dd, J=6.4 Hz, 4.0 Hz, 1H), 7.74 (dd, J=6.4 Hz, 3.3 Hz, 1H), 10.56 (s, 1H)

IR (KBr, cm$^{-1}$): 3450, 3250 (NH)

MS (m/e): 452 (MH+)

Anal. Calcd. for $C_{19}H_{29}Cl_2N_5O_5S_2$: C, 42.07; H, 5.39; N, 12.91%. Found: C, 42.00; H, 5.25; N, 12.75%.

EXAMPLE 4

N-[2-[(1-Methyl-1H-benzimidazol-2-yl)amino]ethyl]-4-[(methylsulfonyl)amino]benzenesulfonamide Hydrochloride Hemihydrate

Step 1) Preparation of N-[2[(1-Methyl-1H-benzimidazol-2-yl)amino]ethyl]acetamide A mixture of 2-methylsulfonyl-1-methyl-1H-benzimidazole (7.0 g, 0.033 mol) and N-acetylethylenediamine (17.0 g, 0.167 mol) was heated at 120°–125° C. for 8 hours. The mixture was cooled, diluted with H$_2$O, made basic (pH8) with 2.5N NaOH, and filtered. The filtrate was extracted with EtOAc, and the combined extracts were washed with brine, dried, and concentrated to give a yellow solid 2.3 g (30%).

NMR (DMSO-d$_6$, 300 MHz): δ1.82 (s, 3H), 3.32 (t, J=6.0 Hz, 2H), 3.40 (t, J=6.0 Hz, 2H), 3.82 (s, 3H), 6.20 (m, 1H), 6.78 (m, 1H), 6.95 (m, 2H), 7.17 (d, J=6.5 Hz, 1H), 8.05 (m, 1H).

Step 2) Preparation of 2-[N-(2-Aminoethyl)amino]-1-methyl-1H-benzimidazole

A mixture of N-[2-[(1-methyl-1H-benzimidazol-2-yl)amino]ethyl]acetamide (2.32 g, 9.98 mmol), 2N HCl (20 mL), and MeOH (20 mL) was heated under reflux for 20 hours. The mixture was concentrated, diluted with H$_2$O, made basic (pH9) with 2.5N NaOH, and extracted with EtOAc. The combined extracts were dried and concentrated to give a brown oil. Purification by flash chromatography (eluent 10% MeOH/CH$_2$Cl$_2$) gave a yellow oil 1.47 g (77%).

NMR (DMSO-d$_6$, 300 MHz): δ2.78 (t, J=6.0 Hz, 2H), 3.38 (t, J=6.0 Hz, 2H), 3.50 (s, 3H), 3.9 (brs, 2H), 6.78 (m, 1H), 6.90 (m, 2H), 7.10 (d, J=6.5 Hz, 1H).

Step 3) Preparation of N-[2-[(1-Methyl-1H-benzimidazol-2-yl)amino]ethyl]-4-[(methylsulfonyl)amino]benzenesulfonamide Hydrochloride Hemihydrate To a stirred solution of 2-[N-(2-aminoethyl)amino]-1-methyl-1H-benzimidazole (1.47 g, 5.59 mmol) and Et$_3$N (0.60 g, 5.59 mmol) in p-dioxane (40 mL) was added 4-[(methylsulfonyl)amino]benzenesulfonyl chloride (1.51 g, 5.59 mmol). After 2 hours, the mixture was concentrated, taken up in H$_2$O, and extracted with EtOAc. The combined extracts were washed with H$_2$O and brine, dried, and concentrated to give an oil. Purification by flash chromatography (eluent 5% MeOH/CH$_2$Cl$_2$) gave a white solid. Saturated methanolic HCl was added and the HCl salt was collected by filtration. Recrystallization from EtOH gave 0.84 g (32%) of product m.p. 140°–142° C.

NMR (DMSO-d$_6$, 400 MHz): δ3.03 (m, 2H), 3.09 (s, 3H), 3.55 (m, 2H), 3.60 (s, 3H), 7.28 (m, 4H), 7.40 (m, 1H), 7.48 (m, 1H), 7.72 (m, 1H), 7.74 (d, J=8.8 Hz, 1H), 7.88 (t, J=6.6 Hz, 1H), 8.98 (s, 1H), 10.40 (s, 1H), 13.34 (s, 1H)

IR (KBr, cm$^{-1}$): 3600 (NH)

MS (m/e): 425 (MH+)

Anal. Calcd. for $C_{17}H_{22}ClN_5O_4S_2 \cdot 0.5 H_2O$: C, 43.46; H, 4.93; N, 14.91%. Found: C, 43.84; H, 4.64; N, 14.92%.

EXAMPLE 5

N-Methyl-N-[2-[(1-methyl-1H-benzimidazol-2-yl)amino]ethyl]-4-[(methylsulfonyl)amino]benzenesulfonamide Hydrochloride Hydrate

Step 1) Preparation of 2-(Methylsulfonyl)-1H-benzimidazole

According to the procedure of B. M. Trost, et al., *Tetrahedron Lett.*, 22 (14), 1287 (1981), to a cooled (0° C.), stirred solution of 2-(methylthio)benzimidazole (14.5 g, 0.088 mol) in MeOH (350 mL) was added a solution of oxone (2 KHSO$_5$·KHSO$_4$·K$_2$SO$_4$; 81.6 g, 0.133 mol) in H$_2$O (350 mL) over 10 minutes. The cooling bath was removed after 10 minutes, stirring was continued at room temperature for 5 hours. The MeOH was removed under reduced pressure and the white solid was collected by filtration to give 15.5 g (89%) of product m.p. 200°–202° C.

NMR (DMSO-d$_6$, 300 MHz): δ3.50 (s, 3H), 7.40 (dd, J=6.2 Hz, 3-1 Hz, 2H), 7.72 (brs, 2H).

Step 2) Preparation of 2-(Methylsulfonyl)-1-methyl-1H-benzimidazole

To a cooled (0° C.), stirred solution of 2-(methylsulfonyl)-1H-benzimidazole (4.60 g, 0.023 mol) in DMF (25 mL) was added NaH (60% dispersion in mineral oil; 0.94 g, 0.023 mol) in several portions. After 1 hour, iodomethane (3.33 g, 0.023 mol) was added. The cooling bath was removed and stirring was continued for 18 hours. The mixture was recooled to 0° C., H$_2$O (75 mL) was added, and the off-white precipitate was collected by filtration to give 4.30 g (88%) of product m.p. 131°–132° C.

NMR (DMSO-d$_6$, 300 MHz): δ3.59 (s, 3H), 4.09 (s, 3H), 7.40 (m, 1H), 7.50 (m, 1H), 7.77 (d, J=8.2 Hz, 1H), 7.82 (d, J=8.1 Hz, 1H).

Step 3) Preparation of 2-[N-[(2-Methylamino)ethyl]amino]-1-methyl-1H-benzimidazole A mixture of 2-(methylsulfonyl)-1-methyl-1H-benzimidazole (5.0 g, 0.024 mol) and N-methylethylenediamine (8.8 g, 0.119 mol) was heated at 120°–130° C. for 12 hours. The mixture was concentrated, taken up in H$_2$O, made basic (pH 10) with 2.5N NaOH; and extracted with EtOAc. The combined extracts were dried and concentrated to give a brown oil. Purification by flash chromatography (eluent 10% MeOH/CH$_2$Cl$_2$) gave 3.0 g (62%) of a yellow oil.

NMR (CDCl$_3$, 300 MHz): δ2.60 (s, 3H), 3.22 (t, J=6.7 Hz, 2H), 3.52 (s, 3H), 3.81 (t, J=6.7 Hz, 2H), 7.10 (m, 4H), 7.35 (m, 1H).

Step 4) Preparation of N-Methyl-N-[2-[(1-methyl-1H-benzimidazol-2-yl)amino]ethyl]-4-[(methylsulfonyl)amino]benzenesulfonamide Hydrochloride Hydrate To a stirred solution of 2-[N-[(2-methylamino)ethyl]-1-methyl-1H-benzimidazole (3.00 g, 14.7 mmol) and Et$_3$N (1.63 g, 16.1 mmol) in p-dioxane (60 mL) was added 4-[(methylsulfonyl)amino]benzenesulfonyl chloride (3.69 g, 14.7 mmol). After 1 hour, the mixture was concentrated, taken up in H$_2$O, and extracted with EtOAc. The extracts were washed with H$_2$O and brine, dried, and concentrated. Purification by flash chromatography (eluent 5% MeOH/CH$_2$Cl$_2$) gave a white solid. Warm methanolic HCl was added and the resulting HCl salt was recrystallized from EtOH/H$_2$O (5:1) to give 1.39 g (20%) of a white solid m.p. 155°–157° C.

NMR (DMSO-d$_6$, 400 MHz): δ2.79 (s, 3H), 3.11 (s, 3H), 3.44 (t, J=5.8 Hz, 2H), 3.63 (s, 3H), 3.68 (m, 2H), 7.27 (m, 2H), 7.36 (m, 2H), 7.43 (dd, J=6.4 Hz, 3.5 Hz, 1H), 7.49 (dd, J=6.4 Hz, 3.1 Hz, 1H), 7.70 (m, 2H), 8.98 (s, 1H), 10.49 (s, 1H), 13.75 (s, 1H)

IR (KBr, cm$^{-1}$): 3600 (NH)

MS (m/e): 439 (MH+)

Anal. Calcd. for C$_{18}$H$_{24}$ClN$_5$O$_4$S$_2$·H$_2$O: C, 43.86; H, 5.31; N, 14.20%. Found: C, 43.92; H, 5.55; N, 14.31%.

EXAMPLE 6

N-Methyl-N-[2-[methyl(1-methyl-1H-benzimidazol-2-yl)amino]ethyl-4-[(methylsulfonyl)amino]benzamide Hydrochloride A mixture of 2-[N-methyl-N-[(2-methylamino)ethyl]amino]-1-methyl-1H-benzimidazole (3.14 g, 0.0144 mol), 4-[(methylsulfonyl)amino]benzoic acid (3.10 g, 0.0144 mol), DCC (2.97 g, 0.0144 mol), 1-hydroxybenztriazole hydrate (1.94 g, 0.0144 mol), DMF (4 mL), and THF (42 mL) was stirred at room temperature for 2.5 days. The mixture was filtered and the filtrate was concentrated. The remaining material was taken up in CHCl$_3$, washed with brine, saturated aqueous NaHCO$_3$, brine, dried (MgSO$_4$) and concentrated to give a brown oil. Purification by flash chromatography (eluent 5% MeOH/CHCl$_3$) gave 5.00 g of a white foam. Saturated methanolic HCl was added and the solution was concentrated to give a white foam. The material was stirred in boiling iPrOH (150 mL) to give a white solid 4.00 g m.p. 209°–212° C. Recrystallization from EtOH gave 2.20 g (34%).

NMR (DMSO-d$_6$, 400 MHz): δ2.96 (s, 3H), 2.99 (s, 3H), 3.38 (brs, 3H), 3.79 (brs, 5H) 3.94 (brs, 2H), 7.09 (m, 4H), 7.34 (m, 2H), 7.48 (m, 1H), 7.60 (m, 1H), 10.02 (s, 1H), 13.87 (brs, 1H)

IR (KBr, cm$^{-1}$): 3440 (NH), 1635 (C=O)

MS (m/e): 416 (MH+)

Anal. Calcd. for C$_{20}$H$_{26}$ClN$_5$O$_3$S: C, 53.15; H, 5.80; N, 15.49%. Found: C, 53.01; H, 5.47; N, 15.88%.

EXAMPLE 7

N-Methyl-N-[2-[methyl(1H-benzimidazol-2-yl)amino]ethyl]-4-[(methylsulfonyl)amino]benzenesulfonamide

Step 1) Preparation of 2-[N-Methyl-N-[(2-methylamino)ethyl]amino-1H-benzimidazole A mixture of 2-chlorobenzimidazole (20.0 g, 0.131 mol), N,N'-dimethylethylenediamine (34.7 g, 0.393 mol), and EtOH (200 mL) was heated under reflux for 36 hours. The mixture was cooled, concentrated, taken up in H$_2$O, and made basic (pH 9–10) with 2.5N NaOH. The mixture was extracted with EtOAc, and the combined extracts were dried and concentrated to give a brown oil. Purification by flash chromatography (eluent 10% MeOH/CH$_2$Cl$_2$) gave 14.2 g (53%) of an orange oil.

NMR (DMSO-d$_6$, 300 MHz): δ2.34 (s, 3H), 2.77 (t, J=6.5 Hz, 2H), 3.05 (t, J=6.5 Hz, 2H), 6.85 (m, 2H), 7.14 (m, 2H).

Step 2) Preparation of N-Methyl-N-[2-[methyl(1H-benzimidazol-2-yl)amino]ethyl]-4-[(methylsulfonyl)amino]benzenesulfonamide Hydrochloride To a stirred mixture of 2-[N-methyl-N-[(2-methylamino)ethyl]amino]-1H-benzimidazole (4.00 g, 19.60 mmol), Et$_3$N (1.98 g, 19.60 mmol), and p-dioxane (80 mL) was added 4-[(methylsulfonyl)amino]benzenesulfonyl chloride (5.28 g, 19.60 mmol). After 1 hour, the resulting solid was collected by filtration and triturated with ether. Warm saturated methanolic HCl was added and the HCl salt was collected by filtration. Trituration with hot EtOH and recrystallization from EtOH/H$_2$O (4:1) gave 2.78 g (30%) of an off-white solid m.p. 150°–152° C.

NMR (DMSO-d$_6$, 400 MHz): δ2.75 (s, 3H), 3.11 (s, 3H), 3.25 (t, J=5.3 Hz, 2H), 3.27 (s, 3H), 3.83 (t, J=5.3 Hz, 2H), 7.26 (m, 2H), 7.33 (m, 2H), 7.41 (m, 2H), 7.68 (d, J=8.8 Hz, 2H), 10.46 (s, 1H), 13.10 (s, 1H)

IR (KBr, cm$^{-1}$): 3400 (NH)

MS (m/e): 438 (4%), 360 (6%), 205 (39%), 144 (100%)

Anal. Calcd. for C$_{18}$H$_{24}$ClN$_5$O$_4$S$_2$: C, 43.95; H, 5.33; N, 14.24%. Found: C, 44.26; H, 5.24; N, 14.29%.

EXAMPLE 8

N-[2-[(Quinolin-2yl)amino]ethyl]-4-[(methylsulfonyl)amino]-benzenesulfonamide Hydrochloride Hydrate

Step 1) Preparation of N-[2-[(Quinolin-2-yl)amino]ethyl]acetamide

A mixture of 2-chloroquinoline (10.00 g, 0.061 mol), N-acetylethylenediamine (6.24 g, 0.061 mol), sodium carbonate (6.48 g, 0.061 mol), and 3-methyl-1-butanol (125 mL) was heated under reflux for 3 days. The mixture was cooled, filtered, and the filtrate was concentrated to give 16.3 g (>100%) of a yellow oil. Purification by flash chromatography (eluent 5% MeOH/CHCl$_3$; 10% MeOH/1% Et$_3$N/CHCl$_3$) gave 6.8 g (49%) of a yellow oil.

NMR (DMSO-d$_6$, 300 MH): δ1.82 (s, 3H), 3.28 (m, 2H), 3.45 (m, 2H), 6.75 (d, J=8.6, 1H), 7.14 (m, 2H), 7.48 (m, 2H), 7.61 (d, J=7.9, 1H), 7.84 (d, J=8.9, 1H), 8.02 (t, 1H).

Step 2) Preparation of N-(Quinolin-2-yl)ethylenediamine

A solution of N-[2-[(quinolin-2-yl)amino]ethyl]acetamide (6.8 g, 0.030 mol) in 2N HCl (45 ml, 0.090 ml) was heated under reflux for 20 hours. The solution was cooled and extracted with EtOAc. The aqueous phase was made basic (pH9) with solid KOH, saturated with NaCl, and extracted with EtOAc. The combined extracts were dried (MgSO$_4$) and concentrated to give 3.89 g (68%) of an off-white solid m.p. 124°–125° C.

NMR (DMSO-d$_6$, 300 MHz): δ3.38 (t, J=6.2, 2H), 3.57 (dt, J=6.0, 6.2 2H), 6.78 (d, J=8.8, 1H), 7.04 (t, J=6.0, 1H), 7.10 (m, 1H), 7.47 (m, 2H), 7.59 (d, J=8.1, 1H), 7.81 (d, J=8.9, 1H).

Step 3) Preparation of N-[2-[(Quinolin-2-yl)amino]ethyl]-4-[(methylsulfonyl)amino]-benzenesulfonamide Hydrochloride Hydrate To a stirred solution of N-(quinolin-2-yl)ethylenediamine (1.90 g, 10.15 mmol) and Et$_3$N (1.14 mL, 8.18 mmol) in CH$_2$Cl$_2$ (200 mL) was added 4-[(methylsulfonyl)amino]benzenesulfonyl chloride (2.21 g, 8.18 mmol). After 4 hours, the solution was washed with brine, dried (MgSO$_4$), and concentrated to give a brown foam. Purification by flash chromatography (eluent 10% MeOH/CHCl$_3$) gave 1.98 g of an off-white foam. Saturated methanolic HCl (20 mL) was added and the mixture was left standing for 2 hours. The resulting colorless crystals (1.17 g) were collected by filtration. Recrystallization from MeOH gave 0.72 g (21%) of product m.p. 150°–154° C.

NMR (DMSO-d$_6$, 400 MHz): δ3.06 (m, 2H), 3.09 (2, 3H), 3.73 (brs, 2H), 7.11 (m, 1H) 7.31 (d, J=8.8, 2H), 7.47 (t, J=7.6, 1H), 7.74 (d, J=8.8, 2H), 7.88 (d, J=7.7, 1H) 7.94 (t, J=5.9, 1H), 8.14 (brs, 1H), 8.26 (d, J=8.4, 1H), 9.85 (brs, 1H), 10.40 (s, 1H), 13.13 (brs, 1H)

IR (KBr, cm$^{-1}$): 1660 (C=N)

MS (m/e): 421 (MH+)

Anal. Calcd. for C$_{18}$H$_{21}$ClN$_4$O$_4$S$_2$.H$_2$O: C, 45.52; H, 4.88; N, 11.80%. Found: C, 45.20; H, 4.62; N, 11.55%.

EXAMPLE 9

N-Methyl-N-[2-[methyl(1-ethyl-1H-benzimidazol-2-yl)amino]ethyl]-4-[(methylsulfonyl)amino]benzenesulfonamide Hydrochloride

Step 1) Preparation of 2-Chloro-1-ethylbenzimidazole

To a cooled (0° C.) stirred suspension of NaH (60% dispersion in mineral oil; 7.08 g, 0.118 mol) in DMF (100 mL) was added 2-chlorobenzimidazole (15.00 g, 0.098 mol). The mixture was warmed to room temperature and stirred for 1 hour. Ethyl iodide (18.40 g, 0.118 mol) was added and stirring was continued for 3 hours. The mixture was poured onto the ice water and the resulting off-white solid was collected by filtration to give 10.0 g (61%) of product m.p. 48°–50° C.

NMR (DMSO-d$_6$, 300 MHz): δ1.3 (t, J=8.6 Hz, 3H), 4.28 (q, J=8.6 Hz, 2H), 7.25 (m, 2H), 7.60 (m, 2H).

Step 2) Preparation of 2-[N-Methyl-N-[(2-methylamino)ethyl]amino]-1-ethyl-1H-benzimidazole A solution of 2-chloro-1-ethylbenzimidazole (3.1 g, 0.0172 mol) in N,N'-dimethylethylendiamine (28 mL, 0.261 mol) was heated under reflux for 22 hours. The mixture was concentrated and dissolved in 10% aqueous HOAc (100 mL) and extracted with EtOAc. The aqueous phase was made basic (pH9) with solid KOH, satured with NaCl, and extracted with EtOAc. The extracts were dried (MgSO$_4$) and concentrated to give 3.1 g (78%) of a brown oil.

NMR (DMSO-d$_6$, 300 MHz): δ1.31 (t, J=7.2, 3H), 2.29 (s, 3H), 2.71 (t, J=6.7, 2H), 2.92 (s, 3H), 3.28 (t, J=6.7, 2H), 4.10 (q, J=7.2, 2H), 7.05 (m, 2H), 7.34 (m, 2H).

Step 3) Preparation of N-Methyl-N-[2-[methyl(1-ethyl-1H-benzimidazol-2-yl)amino]ethyl]-4-[(methylsulfonyl)amino]benzenesulfonamide Hydrochloride To a stirred solution of Et$_3$N (0.90 mL, 6.46 mmol) and 2-[N-methyl-N-[(2-methylamino)ethyl]amino]-1-ethyl-1H-benzimidazole (1.50 g, 6.46 mmol) in CH$_2$Cl$_2$ (160 mL) was added 4-[(methylsulfonyl)amino]benzenesulfonyl chloride (1.74 g, 6.46 mmol). After 1.5 hours the solution was washed with brine, dried (MgSO$_4$), and concentrated to give a white foam. Purification by flash chromatography (eluent 5% MeOH/CHCl$_3$; 10% MeOH/CHCl$_3$) gave 2.31 g of a white foam. Saturated methanolic HCl (23 mL) was added and the solution was concentrated to give a brown foam. Recrystallization from iPrOH, then from EtOH gave 1.05 g (32%) of a white solid m.p. 185°–186° C.

NMR (DMSO-d$_6$, 400 MHz): δ1.43 (t, J=7.2, 3H), 2.69 (s, 3H), 3.12 (s, 3H), 3.29 (t, J=5.6, 2H), 3.36 (s, 3H), 3.84 (t, J=5.6, 2H), 4.32 (q, J=7.2, 2H), 7.35 (m, 4H), 7.51 (m, 1H), 7.66 (dd, J=6.4, 2.7, 1H), 7.71 (d, J=8.8, 2H), 10.52 (s, 1H), 13.90 (brs, 1H)

IR (KBr, cm$^{-1}$): 3420 (NH), 1620 (C=N)

MS (m/e): 466 (MH+)

Anal. Calcd. for C$_{20}$H$_{28}$ClN$_5$O$_4$S$_2$: C, 47.85; H, 5.62; N, 13.95%. Found: C, 47.90; H, 5.38; N, 13.84%.

EXAMPLE 10

N-Methyl-N-[2-[methyl[(1-methyl-1H-benzimidazol-2-yl)methyl]-amino]ethyl]-4-[(methylsulfonyl)amino]benzamide Dihydrochloride

Step 1) Preparation of 2-Chloromethyl-1-methyl-1H-benzimidazole

According to the procedure of H. Skolnik, et al., *J. Chem. Soc.*, 65 (1943), a solution of N-methyl-o-phenylenediamine dihydrochloride (16.9 g, 0.087 mol) and chloroacetic acid (12.3 g, 0.130 mol) in 2N HCl (87 mL, 0.173 mol) was heated under reflux for 18 hours. The mixture was cooled, made basic (pH9) with 2.5N NaOH and the precipitate was collected by filtration. Recrystallization from ether/acetone gave 2.06 g of a pale green solid m.p. 143°–145° C. NMR analysis showed the material to be 2-hydroxymethyl-1-methyl-1H-benzimidazole. The filtrate from the above recrystallization was concentrated and purified by flash chromatography (eluent 5% MeOH/CHCl$_3$ to give 5.9 g (38%) of a yellow solid m.p. 95°–96° C.

NMR analysis showed the material to be 2-chloromethyl-1-methyl-1H-benzimidazole.

NMR (DMSO-d$_6$, 300 MHz): δ3.84 (s, 3H), 5.06 (s, 2H), 7.25 (m, 2H), 7.57 (d, J=7.3), 7.62 (d, J=7.8, 1H).

Step 2) Preparation of 2-[[N-Methyl-N-[(2-methylamino)ethyl]amino]methyl]-1-methyl-1H-benzimidazole To a stirred solution of 2-chloromethyl-1-methyl-1H-benzimidazole (5.8 g, 0.0321 mol) in EtOH (30 mL) was added N,N'-dimethylethylenediamine (14.2 g, 0.161 mol). After 18 hours, the mixture was concentrated, taken up in 10% aqueous HOAc (100 mL) and extracted with ether. The aqueous phase was made basic (pH9) with solid KOH and extracted with EtOAc. The combined extracts were dried (MgSO$_4$) and concentrated to give 5.3 g (71%) of a yellow oil.

NMR (DMSO-d$_6$, 300 MHz): δ2.20 (s, 3H), 2.24 (s, 3H), 2.50 (m, 2H), 2.58 (m, 2H), 3.78 (s, 2H), 3.85 (s, 3H), 7.21 (m, 2H), 7.53 (d, J=8.5, 1H), 7.60 (d, J=7.9, 1H).

Step 3) Preparation of N-Methyl-N-[2-[methyl[(1-methyl-1H-benzimidazol-2-yl)methyl]amino]ethyl]-4-[(methylsulfonyl)amino]benzamide Dihydrochloride A solution of 2-[[N-methyl-N-[(2-methylamino)ethyl]amino]methyl]-1-methyl-1H-benzimidazole (2.70 g, 0.0116 mol), 4-[(methylsulfonyl)amino]benzoic acid (2.50 g, 0.0116 mol) DCC (2.40 g, 0.0116 mol), and 1-hydroxybenztriazole hydrate (1.57 g, 0.0116 mol) in THF (35 mL) was stirred at room temperature for 2.5 days. The mixture was filtered and diluted with EtOAc (100 mL). The solution was washed with saturated aqueous NaHCO₃, brine, dried (MgSO₄), and concentrated to give a brown foam. Purification by flash chromatography (eluent 5% MeOH/CHCl₃) gave 4.5 g of a white foam. Saturated methanolic HCl (45 mL) was added and the solution was concentrated to give a white foam. The foam was taken up in EtOH and boiled until a precipitate formed. Recrystallization from EtOH/H₂O gave 1.75 g (30%) of a white solid m.p. 208°–210° C.

NMR (DMSO-d₆, 400 MHz): $\delta$2.98 (s, 3H), 3.04 (s, 3H), 3.55 (brs, 2H), 3.89 (brs, 3H), 3.96 (s, 3H), 4.60 (brs, 2H), 4.82 (brs, 2H), 7.23 (d, J=8.5, 2H), 7.44 (m, 4H), 7.73 (d, J=7.9, 1H), 7.76 (d, J=8.0, 1H), 10.10 (s, 1H)

IR (KBr, cm⁻¹): 3440(NH), 1625 (C=O)

MS (m/e): 430 (MH⁺)

Anal. Calcd. for $C_{21}H_{29}Cl_2N_5O_3S$: C, 50.20; H, 5.82; N, 13.94%. Found: C, 50.13; H, 5.84; N, 13.72%.

EXAMPLE 11

N-Methyl-N-[3-[methyl(1-methyl-1H-benzimidazol-2-yl)amino]propyl]-4-[(methylsulfonyl)amino]benzenesulfonamide Hydrochloride Step 1) Preparation of 2-[N-Methyl-N-[(2-methylamino)propyl)amino]-1-methyl-1H-benzimidazole A mixture of 2-chloro-1-methylbenzimidazole (2.72 g, 16.4 mmol), N,N'-dimethyl-1,3-propanediamine (10.05 g, 98.4 mmol), and nBuOH (100 mL) was heated under reflux for 20 hours. The mixture was concentrated, taken up in H₂O, and made basic (pH 9–10) with 2.5N NaOH. The mixture was extracted with EtOAc, and the combined extracts were dried and concentrated. Purification by flash chromatography (eluent Et₃N-/MeOH/CH₂Cl₂, 1:10:84) gave 3.37 g (89%) of an orange oil.

NMR (DMSO-d₆, 300 MHz): $\delta$1.85 (m, 2H), 2.39 (s, 3H), 2.72 (t, J=6.1, 2H), 2.97 (s, 3H), 3.38 (t, J=6.2, 2H), 3.61 (s, 3H), 7.07 (m,2H), 7.32 (m, 2H).

Step 2) Preparation of N-Methyl-N-[3-[methyl(1-methyl-1H-benzimidazol-2-yl)amino]propyl]-4-[(methylsulfonyl)amino]benzenesulfonamide Hydrochloride To a stirred mixture of 2-[N-methyl-N-[(2-methylamino)propyl]amino]-1-methyl-1H-benzimidazole (1.61 g, 6.93 mmol), Et₃N (0.70 g, 6.93 mmol), and dioxane (30 mL) was added 4-(methylsulfonyl)aminobenzenesulfonyl chloride (1.87 g, 6.93 mmol). After 1 hour, the mixture was concentrated, taken up in H₂O, and extracted with EtOAc. The extracts were washed with H₂O and brine, dried, and concentrated to give an off-white solid. Warm saturated methanolic HCl (30 mL) was added and the resulting white solid was collected by filtration to give 1.25 g (36%) of product m.p. 233°–234° C.

NMR (DMSO-d₆, 400 MHz): $\delta$1.91 (m, 2H), 2.64 (s, 3H), 2.98 (t, J=6.6 Hz, 2H), 3.11 (s, 3H), 3.27 (s, 3H), 3.59 (t, J=6.9 Hz, 2H), 3.79 (s, 3H), 7.35 (m, 4H), 7.47 (dd, J=4.8 Hz, 1.8 Hz, 1H), 7.60 (dd, J=4.8 Hz, 1.8 Hz, 1H), 7.69 (m, 2H), 10.50 (s, 1H), 13.65 (s, 1H)

IR (KBr, cm⁻¹): 3400 (NH)

MS (m/e): 466 (MH⁺)

Anal. Calcd. for $C_{20}H_{28}ClN_5O_4S_2$: C, 47.85; H, 5.62; N, 13.95%. Found: C, 47.92; H, 5.54; N, 13.87%.

EXAMPLE 12

N-[4-[[4-(1-Methyl-1H-benzimidazol-2-yl)-1-piperazinyl]sulfonyl]phenyl]methanesulfonamide Hydrochloride Step 1) Preparation of 2-N-(1-Piperazinyl)-1-methyl-1H-benzimidazole A mixture of 2-chloro-1-methylbenzimidazole (3.50 g, 0.021 mol), piperazine (10.86 g, 0.126 mol), and n-BuOH (100 mL) was heated under reflux for 24 hours. The mixture was concentrated, taken up in H₂O, and made basic (pH 9–10) with 2.5N NaOH. The aqueous mixture was extracted with EtOAc, and the extracts were dried and concentrated. Purification by flash chromatography (eluent 10% MeOH/CH₂Cl₂) gave 3.63 g (80%) of a yellow solid m.p. 95°–96° C.

NMR (DMSO-d₆, 300 MHz): $\delta$2.96 (m, 4H), 3.17 (m, 4H), 3.60 (s, 3H), 4.10 (s, 1H), 7.10 (m, 3H), 7.40 (dd, J=3.9 Hz, 1.4 Hz, 1H).

Step 2) Preparation of N-[4-[[4-(1-Methyl-1H-benzimidazol-2-yl)piperazinyl]sulfonyl]phenyl]methanesulfonamide Hydrochloride To a stirred solution of 2-N-(1-piperazinyl)-1-methyl-1H-benzimidazole (4.09 g, 18.91 mmol) and Et₃N (2.10 g, 20.80 mmol) in p-dioxane (100 mL) was added 4-(methylsulfonyl)aminobenzenesulfonyl chloride (5.10 g, 18.91 mmol). After 1 hour, the mixture was concentrated, suspended in H₂O, and filtered. The resulting solid was triturated with EtOH. Saturated methanolic HCl (20 mL) was added and the solid was collected by filtration. Recrystallization from EtOH/H₂O (3:1) gave 4.51 g of an off-white solid.

NMR (DMSO-d₆, 400 MHz): $\delta$3.13 (s, 4H), 3.14 (s, 3H), 3.65 (s, 4H), 3.66 (s, 3H), 7.32 (m, 1H), 7.36 (m, 1H), 7.40 (m, 2H), 7.49 (dd, J=4.4 Hz, 1.8 Hz, 1H), 7.60 (dd, J=4.4 Hz, 2.3 Hz, 1H), 7.74 (m, 2H), 10.60 (s, 1H)

IR(KBr, cm⁻¹: 3400 (NH)

MS (m/e): 450 (MH⁺)

Anal. Calcd. for $C_{19}H_{24}ClN_5O_4S_2$: C, 46.96; H, 4.98; N, 14.41%. Found: C, 46.77; H, 4.91; N, 14.21%.

EXAMPLE 13

N-Methyl-N-[2-[methyl(1-methyl-1H-benzimidazol-2-yl)methyl]amino]ethyl-4-[(methylsulfonyl)amino]benzenesulfonamide Dihydrochloride To a stirred solution of 2-[[N-methyl-N-[(2-methylamino)ethyl]amino]methyl]-1-methyl-1H-benzimidazole (2.55 g, 0.0110 mol) and Et₃N(1.53 mL, 0.0110 mol) in CH₂Cl₂ (50 mL) was added 4-[(methylsulfonyl)amino]benzenesulfonyl chloride (2.96 g, 0.0110 mol). After 4 hours, the mixture was diluted to 150 mL with CH₂Cl₂, washed with saturated aqueous NaHCO₃, dried (MgSO₄), and concentrated to give an off-white foam. Purification by flash chromatography (eluent 5% MeOH/CHCl₃) gave 4.9 g of a white foam. Saturated methanolic HCl (50 mL) was added and the solution was concentrated to give an off-white foam. The foam was stirred in boiling EtOH until a precipitate formed. Recrystallization from EtOH/H₂O (twice) gave 2.46 g (42%) of a white solid m.p. 157°–160° C.

NMR (DMSO-d₆, 400 MHz): $\delta$2.70 (s, 3H), 2.89 (s, 3H), 3.13 (s, 3H), 3.36 (m, 2H), 3.43 (m, 2H), 3.94 (s, 3H), 4.71 (s, 2H), 7.39 (m, 4H), 7.75 (m, 4H), 10.57 (s, 1H)

IR (KBr, cm⁻¹): 3400 (NH), 1590 (C=N)

MS (m/e): 466 (MH+)

Anal. Calcd. for $C_{20}H_{29}Cl_2N_5O_4S_2$: C, 44.61; H, 5.43; N, 13.00%. Found: C, 44.27; H, 5.81; N, 12.79%.

EXAMPLE 14

N-Methyl-N-[2-[methyl(quinolin-2-yl)amino]ethyl]-4-[(methylsulfonyl)amino]benzenesulfonamide Hydrochloride Step 1) Preparation of 2-[N-Methyl-N-[(2-methylamino)ethyl]amino]quinoline A solution of 2-chloroquinoline (5.00 g, 0.0306 mol) in N,N'-dimethylethylenediamine (25 mL, 0.235 mol) was heated under reflux for 20 hours, cooled, and concentrated. 10% aqueous HOAc (100 mL) was added and the mixture was filtered. The filtrate was extracted with EtOAc, and the aqueous phase was made basic (pH9) with solid KOH. The mixture was saturated with NaCl and extracted with EtOAc. The combined extracts were dried (MgSO$_4$) and concentrated to give 6.0 g (91%) of a yellow oil.

NMR (DMSO-d$_6$, 300 MHz): δ2.30 (s, 3H), 2.69 (t, J=6.7, 2H), 3.15 (s, 3H), 3.67 (t, J=6.7, 2H), 7.06 (d, J=9.2, 1H), 7.15 (m, 1H), 7.50 (M, 2H), 7.65 (dd, J=7.6, 1.0, 1H), 7.97 (d, J=9.2, 1H).

Step 2) Preparation of N-Methyl-N-[2-[methyl(quinolin-2-yl)amino]ethyl]-4-[(methylsulfonyl)amino]benzenesulfonamide Hydrochloride To a stirred solution of 2-[N-methyl-N-[(2-methylamino)ethyl]amino]quinoline (3.00 g, 0.0139 mol) and Et$_3$N (1.94 mL, 0.0139 mol) in CH$_2$Cl$_2$ (350 mL) was added 4-[(methylsulfonyl)amino]benzenesulfonyl chloride (3.76 g, 0.0139 mol). After 20 hours, the mixture was washed with brine, dried (MgSO$_4$), and concentrated. Purification by flash chromatography (eluent 5% MeOH/CH$_2$Cl$_2$) gave 5.5 g of a white foam. Saturated methanolic HCl (70 mL) was added. The mixture was concentrated, triturated with hot MeOH, and dried to give 5.01 g (74%) of a white solid m.p. 268°–269° C.

NMR (DMSO-d$_6$, 400 MHz): δ2.77 (s, 3H), 3.11 (s, 3H), 3.27 (m, 2H), 3.39 (s, 3H), 3.44 (m, 2H), 4.06 (brs, 1H), 7.33 (d, J=8.7, 2H), 7.51 (m, 2H), 7.67 (d, J=8.7, 2H), 7.79 (m, 1H), 7.94 (m, 1H), 8.43 (m, 1H)

IR (KBr, cm$^{-1}$): 3400 (NH), 1640 (C=N)

MS (m/e): 449 (MH+)

Anal. Calcd. for $C_{20}H_{25}ClN_4O_4S_2$: C, 49.53; H, 5.20; N, 11.55%. Found: C, 49.36; H, 5.02; N, 11.59%.

EXAMPLE 15

N-[4-(1-Methyl-1H-benzimidazol-2-yl]-1-piperazinyl]-4-[(methylsulfonyl)amino]benzamide Hydrochloride Hemihydrate A mixture of 2-N-(1-piperazinyl)-1-methyl-1H-benzimidazole (2.20 g, 10.17 mmol), 4-(methylsulfonyl)aminobenzoic acid (2.19 g, 10.17 mmol), 1-hydroxybenztriazole hydrate (1.37 g, 30.52 mmol), dicyclohexylcarbodiimide (1.95 g, 10.17 mmol), DMF (30 mL), and THF (50 mL) was stirred at room temperature for 2 days. The mixture was filtered and the filtrate was concentrated, taken up in H$_2$O, and extracted with EtOAc. The combined extracts were washed with H$_2$O, saturated aqueous NaHCO$_3$, brine, dried, and concentrated. Trituration with EtOH gave an off-white solid. The HCl salt was made with saturated methanolic HCl and was recrystallized from EtOH/H$_2$O (3:1) to give 1.95 g (38%) of a white solid m.p. 225°–256° C.

NMR (DMSO-d$_6$, 400 MHz): δ3.06 (s, 3H), 3.89 (brs, 4H), 3.68 (s, 4H), 3.75 (s, 3H), 7.28 (m, 1H), 7.30 (m, 1H), 7.37 (m, 2H), 7.47 (m, 2H), 7.54 (m, 1H), 7.64 (dd, J=7.5 Hz, 2.3 Hz, 1H), 10.12 (s, 1H)

IR (KBr, cm$^{-1}$): 3600–3200 (NH), 1625 (CO)

MS (m/e): 414 (MH+)

Anal. Calcd. for $C_{20}H_{24}ClN_5O_3S\cdot 0.5\ H_2O$: C, 52.34; H, 5.49; N, 15.26%. Found: C, 52.20; H, 5.17; N, 15.36%.

EXAMPLE 16

N-Methyl-N-[2-[methyl[5-[(methylsulfonyl)amino]-1H-benzimidazol-2-yl]amino]ethyl]benzamide Step 1) Preparation of 2-Hydroxy-5-nitro-1H-benzimidazole According to the procedure of A. T. James, et al., *J. Chem. Soc.*, 1515, (1950), to cooled (0° C.), stirred nitric acid (300 mL) was added all at once 2-hydroxy-1H-benzimidazole. After 1 minute a yellow precipitate had formed. The cooling bath was removed and stirring was continued for 10 minutes. The mixture was poured onto ice, and the off-white solid was collected by filtration and dried under vacuum at 60° C. to give 25.1 g (94%) of product m.p. >300° C.

NMR (DMSO-d$_6$, 300 MHz): δ7.09 (d, J=8.6, 1H), 7.70 (d, J=2.3, 1H), 7.93 (dd, J=8.6, 2.3, 1H), 11.17 (s, 1H), 11.40 (s, 1H).

Step 2) Preparation of 2-Chloro-5-nitro-1H-benzimidazole

According to the procedure of A. T. James, et al., *J. Chem. Soc.*, 1515 (1950), a mixture of 2-hydroxy-5-nitro-1H-benzimidazole (10.0 g, 0.0558 mol) and phosphoryl chloride (100 mL) was heated under reflux for 3 hours. The mixture was cooled, concentrated, and ice water was added. The resulting precipitate was collected by filtration. NMR analysis showed the material to be a 1:1 mixture of starting material and product. (Note: Longer heating does not improve the conversion.) Purification by flash chromatography (material preadsorbed onto silica; eluent 40% EtOAc/hexane) gave 4.4 g (40%) of the off-white solid product m.p. 215°–217° C.

NMR (DMSO-d$_6$, 300 MHz): δ7.68 (d, J=8.9, 1H), 8.12 (dd, J=8.9, 2.3, 1H), 8.39 (d, J=2.3, 1H), 14.00 (brs, 1H).

Step 3) Preparation of 2-[N-Methyl-N-[(2-methylamino)ethyl]amino]-5-nitro-1H-benzimidazole A solution of 2-chloro-5-nitro-1H-benzimidazole (7.5 g, 0.038 mol) in N,N'-dimethylethylenediamine (30.1 mL, 0.284 mol) was heated under reflux for 5 hours. The mixture was concentrated, taken up in 10% aqueous HOAc (200 mL) and extracted with EtOAc. The aqueous phase was filtered and made basic (pH8) with solid NaOH. The resulting orange solid 9.1 g (96%) collected by filtration had m.p. 112°–114° C.

NMR (DMSO-d$_6$, 300 MHz): δ2.31 (s, 3H), 2.73 (t, J=6.3, 2H), 3.13 (s, 3H), 3.57 (t, J=6.3, 2H), 7.22 (dd, J=8.5, 0.4, 1H), 7.87 (m, 2H).

Step 4) Preparation of N-Methyl-N-[2-[methyl(5-nitro-1H-benzimidazol-2-yl)amino]ethyl]benzamide To a stirred solution of 2-[N-methyl-N-[(2-methylamino)ethyl]amino]-5-nitro-1H-benzimidazole (1.00 g, 4.01 mmol) and Et$_3$N (0.426 g, 4.21 mmol) in THF (20 mL) was added benzoyl chloride (0.592 g, 4.21 mmol). After 1 hour, the mixture was diluted with EtOAc, washed with brine, saturated aqueous NaHCO$_3$, brine, dried (MgSO$_4$) and concentrated to give 1.3 g (92%) of a yellow solid.

NMR (DMSO-d$_6$, 300 MHz): δ2.95 and 3.05 (s, 3H), 3.19 and 3.30 (s, 3H), 3.55, 3.65, 3.75, and 3.85 (s, 4H), 7.00–7.30 (m, 6H), 7.80 (m, 2H).
Note: The compound exists as a mixture of amide rotamers. The NMR peaks for both rotamers are listed above.

Step 5) Preparation of N-Methyl-N-[2-[methyl(5-amino-1H-benzimidazol-2-yl)amino]ethyl]benzamide A mixture of N-methyl-N-[2-[methyl(5-nitro-1H-benzimidazol-2-yl)amino]ethyl]benzamide (1.30 g, 3.68 mmol) and SnCl$_2$.2H$_2$O (4.15 g, 18.39 mmol) in EtOH (15 mL) was heated under reflux for 1 hour. The mixture was cooled and made basic (pH8) with 2.5N NaOH. The precipitate was removed by filtration and the filtrate was concentrated. The residue was stirred with EtOAc (150 mL) overnight, dried (MgSO$_4$), and concentrated to give 1.12 g (94%) of a green foam.

NMR (DMSO-d$_6$, 300 MHz): δ2.70–3.10 (m, 6H), 3.30–3.70 (m, 4H), 6.20 (m, 1H), 6.42 (m, 1H), 6.80 (m, 1H), 7.20 (m, 5H).
Note: The compound exists as a mixture of amide rotamers.

Step 6) Preparation of N-Methyl-N-[2-[methyl[5-[(methylsulfonyl)amino]-1H-benzimidazol-2-yl]amino]ethyl]benzamide To a cooled (0° C.) stirred solution of N-methyl-N-[2-[methyl(5-amino-1H-benzimidazol-2-yl)amino]ethyl]benzamide (1.10 g, 3.40 mmol) and Et$_3$N (0.50 mL, 3.57 mmol) in THF (20 mL) was added MsCl (0.41 g, 3.57 mmol). The cooling bath was removed and stirring was continued for 1.5 hours. Brine was added and the mixture was extracted with EtOAc. The extracts were dried (MgSO$_4$) and concentrated to give a green foam. Purification by flash chromatography (eluent 5% MeOH/CHCl$_3$; 10% MeOH/CHCl$_3$) and again (eluent 7.5% MeOH/CHCl$_3$) gave 863 mg of a green foam. Saturated methanolic HCl (10 mL) was added and the solution was concentrated to give a yellow foam. The foam was heated in EtOH/iPrOH (1 mL/10 mL) to give 400 mg (27%) of an off-white solid m.p. 264°–265° C. (dec.).

NMR (DMSO-d$_6$, 400 MHz): δ2.91, 2.97, 3.00 and 3.05 (s, 6H), 3.25 (s, 3H), 3.58, 3.69, 3.77, and 3.92 (brs, 4H), 7.00–7.40 (m, 8H), 9.75 (s, 1H), 13.20 (brs, 1H).
Note: The compound exists as a mixture of amide rotamers.

IR (KBr, cm$^{-1}$): 3400, 3200 (NH), 1650 (C=O)
MS (m/e): 402 (MH+)
Anal. Calcd. for C$_{19}$H$_{24}$ClN$_5$O$_3$S: C, 52.11; H, 5.52; N, 15.99%. Found: C, 52.20; H, 5.50; N, 15.60%.

EXAMPLE 17

N-Methyl-N-[2-(2-methylamino-1H-benzimidazol-1-yl)ethyl]-4-[(methylsulfonyl)amino]benzenesulfonamide Hydrochloride

Step 1) Preparation of 2-(2-Nitroanilino)ethanol

According to the procedure of B. Agai, et al., *Tetrahedron*, 32, 839, (1976), a solution of 1-chloro-2-nitrobenzene (50.0 g, 0.317 mol) and 2-aminoethanol (116.3 g, 1.904 mol) in nBuOH (400 mL) was heated under reflux for 6 hours. The mixture was concentrated, taken up in H$_2$O, and extracted with ether. The organic phase was washed with brine, dried, and concentrated to give 43.1 g (75%) of an orange solid m.p. 78° C.

NMR (DMSO-d$_6$, 300 MHz): δ3.40 (t, J=5.4 Hz, 2H), 3.65 (t, J=5.4 Hz, 2H), 4.98 (s, 1H), 6.70 (dd, J=6.5 Hz, 2.2 Hz, 1H), 7.08 (m, 1H), 7.55 (m, 1H), 8.10 (dd, J=7.2 Hz, 2.5 Hz, 1H), 8.21 (s, 1H).

Step 2) Preparation of 2-(2-Aminoanilino)ethanol

According to the procedure of B. Agai, et al., *Tetrahedron*, 32, 839, (1976), a mixture of 2-(2-nitroanilino)ethanol (43.1 g, 0.237 mol), SnCl$_2$.2 H$_2$O (267.0 g, 1.18 mol), and EtOH (400 mL), was heated under reflux for 4 hours. The mixture was cooled, made basic (pH8) with 2.5N NaOH, and filtered through Celite. The filtrate was concentrated to remove the EtOH and the aqueous phase was extracted with EtOAc. The combined extracts were washed with H$_2$O and brine, dried, and concentrated. Recrystallization from EtOH gave 31.0 g (86%) of a brown solid m.p. 105°–106° C.

NMR (DMSO-d$_6$, 300 MHz): δ3.10 (t, J=5.6 Hz, 2H), 3.61 (s, 2H), 4.42 (s, 2H), 4.70 (t, J=5.6 Hz, 2H), 6.40–6.60 (m, 4H).

Step 3) Preparation of 1-(2-Hydroxyethyl)-2-methylamino-1H-benzimidazole

According to the procedure of B. Agai, et al., *Tetrahedron*, 32, 839, (1976), to a cooled (0° C.), stirred suspension of 2-(2-aminoanilino)ethanol (30.4 g, 0.200 mol) in MeOH (100 mL) was added a solution of CH$_3$NCS (14.6 g, 0.200 mol) in MeOH (60 mL) dropwise. The resulting mixture was stirred at room temperature for 4 hours and then heated under reflux for 15 minutes. CH$_3$I (28.4 g, 0.200 mol) was added and the mixture was heated under reflux for 10 minutes, cooled to room temperature and stirred for 2 hours. Ether (200 mL) was added and the resulting precipitate was collected by filtration, taken up in nBuOH (140 mL), and heated under reflux for 10 hours. The mixture was cooled in the freezer for 3 hours and the white crystals were filtered. The material was dissolved in H$_2$O and the solution was neutralized with 10% aqueous K$_2$CO$_3$. The white solid was collected by filtration to give 8.2 g (21%) of product m.p. >200° C.

NMR(DMSO-d$_6$, 300 MHz): δ2.89 (d, J=4.7 Hz, 3H), 3.65 (m, 2H), 3.99 (t, J=5.5 Hz, 2H), 4.97 (t, J=5.6 Hz, 1H), 6.43 (q, J=4.7 Hz, 1H), 6.90 (m, 2H), 7.15 (m, 2H).

Step 4) Preparation of 2-[2-Methylamino(benzimidazol-1-yl)]ethyl Methanesulfonate To a cooled (0° C.), stirred mixture of 1-(2-hydroxyethyl)-2-methylamino-1H-benzimidazole (8.05 g, 42.12 mmol), Et$_3$N (4.26 g, 42.12 mmol), and CH$_2$Cl$_2$ (85 mL) was added a solution of MsCl (4.83 g, 42.12 mmol) in CH$_2$Cl$_2$ (10 mL). After 2 hours, H$_2$O was added and the layers were separated. The aqueous phase was extracted with CH$_2$Cl$_2$. The combined extracts were washed with brine, dried, and concentrated to give 8.00 g (71%) of a white solid m.p. 48°–50° C.

NMR (DMSO-d$_6$, 300 MHz): δ2.95 (d, J=4.7 Hz, 3H), 3.00 (s, 3H), 4.32(t, J=5.5 Hz, 2H), 5.41(t, J=5.5 Hz, 2H), 6.70 (q, J=4.7 Hz, 1H), 6.95 (m, 2H), 7.10 (m, 2H).

Step 5) Preparation of 1-[(2-Methylamino)ethyl]-2-methylamino-1H-benzimidazole A solution of 2-[2-methylamino(benzimidazol-1-yl)]ethyl methanesulfonate (8.0 g, 29.7 mmol) and 33% CH$_3$NH$_2$/EtOH (60 mL) in EtOH (40 mL) was stirred at room temperature for 4 days. The mixture was concentrated, made basic (pH10) with 2.5N NaOH, and extracted with EtOAc. The combined extracts were dried and concentrated to give a colorless oil. Purification by flash chromatography (eluent Et$_3$N/MeOH/CH$_2$Cl$_2$, 1:10:84) gave 4.20 g (70%) of an oil.

NMR (DMSO-d$_6$, 300 MHz): δ2.32 (s, 3H), 2.75 (t, J=5.5 Hz, 2H), 2.93 (s, 3H), 3.37 (s, 1H), 3.98 (t, J=5.5 Hz, 2H), 6.78 (s, 1H), 6.90 (m, 2H), 7.18 (m, 2H).

Step 6) Preparation of N-Methyl-N-[2-(2-methylamino-1H-benzimidazol-1-yl)ethyl]-4-[(methylsulfonyl)amino]benzenesulfonamide Hydrochloride To a stirred solution of 1-[(2-methylamino)ethyl]-2-methylamino-1H-benzimidazole (2.00 g, 9.94 mmol) and Et$_3$N (1.01 g, 9.94 mmol) in CH$_2$Cl$_2$ (30 mL) was added 4-[(methylsulfonyl)amino]benzenesulfonyl chloride (2.68 g, 9.94 mmol). After 1 hour, H$_2$O was added and the resulting precipitate was collected by filtration. Warm methanolic HCl (50 mL) was added, the resulting solution was concentrated, and the solid was triturated with EtOH. Recrystallization from EtOH/H$_2$O (4:1) gave 3.28 g (70%) of a white solid m.p. 291°–292° C.

NMR (DMSO-d$_6$, 400 MHz): δ2.76 (s, 3H), 3.05 (d, J=4.7 Hz, 3H), 3.11 (s, 3H), 3.29 (t, J=5.5 Hz, 2H), 3.34 (s, 3H), 4.39 (t, J=5.5 Hz, 2H), 7.30 (m, 4H), 7.42 (dd, J=7.1 Hz, 0.9 Hz, 1H), 7.51 (m, 1H), 7.57 (m, 2H), 9.30 (s, 1H), 10.48 (s, 1H), 13.22 (s, 1H)

IR (KBr, cm$^{-1}$): 3400 (NH), 1670 (C=N)

MS (m/e): 438 (MH$^+$)

Anal. Calcd. for C$_{18}$H$_{24}$ClN$_5$O$_4$S$_2$: C, 45.61; H, 5.10; N, 14.77%. Found: C, 45.62; H, 5.18; N, 14.87%.

EXAMPLE 18

N-Methyl-N-[2-(2,3-dihydro-1H-imidazo[1,2-a]benzimidazol-1-yl)ethyl]4-[(methylsulfonyl)amino]benzenesulfonamide Hydrochloride

Step 1) Preparation of 2-[N-bis(2-Hydroxyethyl)amino]-1H-benzimidazole

According to the procedure of V. A. Anisimova, et al., *Khim. Farm. Zh.*, 22 (10), 1212, (1988), a solution of 2-chloro-1H-benzimidazole (5.00 g, 0.0328 mol) and diethanolamine (8.61 g, 0.0819 mol) in 3-methyl-1-butanol (75 mL) was heated under reflux for 44 hours. The mixture was cooled, concentrated, combined with material similarly derived from 1.00 g of starting material, and taken up in 10% aqueous HOAc (150 mL). The mixture was filtered and extracted with EtOAc. The aqueous phase was made basic (pH8) with solid KOH. The resulting white precipitate was collected by filtration to give 4.39 g (50%) of product m.p. 199°–202° C.

NMR (DMSO-d$_6$, 300 MHz): δ3.55 (m, 4H), 3.61 (m, 4H), 5.0 (brs, 2H), 6.84 (m, 2H), 7.11 (m, 2H).

Step 2) Preparation of 1-N-(2-Chloroethyl)-2,3-dihydro-1H-imidazo[1,2-a]benzimidazole According to the procedure of V. A. Anisimova, et al., *Khim. Farm. Zh.*, 22 (10), 1212, (1988), to a stirred suspension of 2-[N-bis(2-hydroxyethyl)amino]-1H-benzimidazole (2.78 g, 12.56 mmol) in DMF (12 mL) was added thionyl chloride (5.08 g, 42.72 mmol). The mixture was heated under reflux for 1 hour, cooled, and poured onto ice (25 g). The mixture was made basic (pH9) with 2.5N NaOH and extracted with CHCl$_3$. The extracts were dried (MgSO$_4$) and concentrated to give a dark brown solid. Purification by flash chromatography (eluent CHCl$_3$) gave 1.71 g (62%) of a brown solid m.p. 110°–112° C.

NMR (DMSO-d$_6$, 300 MHz): δ3.64 (t, J=6.2, 2H), 3.91 (t, J=6.2, 2H), 4.01 (m, 2H), 4.14 (m, 2H), 6.94 (m, 2H), 7.13 (m, 1H), 7.20 (m, 1H).

Step 3) Preparation of 1-N-(2-Iodoethyl)-2,3-dihydro-1H-imidazo[1,2-a]benzimidazole A mixture of NaI (1.73 g, 11.57 mmol) and 2-butanone (20 mL) was heated under reflux for 30 minutes 1-N-(2-Chloroethyl)-2,3-dihydro-1H-imidazo[1,2-a]benzimidazole (1.70 g, 7.71 mmol) and additional 2-butanone (5 mL) were added and heating was continued for 5 hours. EtOAc (50 mL) was added and the mixture was filtered. The filtrate was washed with H$_2$O, 10% sodium bisulfite (25 mL), saturated aqueous NaHCO$_3$, dried (MgSO$_4$) and concentrated to give 2.2 g (92%) of a light brown solid m.p. 101°–103° C.

NMR (DMSO-d$_6$, 300 MHz): δ3.50 (t, J=6.3, 2H), 3.64 (t, J=6.3, 2H), 3.98 (m, 2H), 4.14 (m, 2H), 6.94 (m, 2H), 7.13 (m, 1H), 7.21 (m, 1H).

Step 4) Preparation of [2-(2,3-dihydro-1H-imidazo-[1,2-a]benzimidazole-1-yl)ethyl]acetate According to the procedure of N. Ono, et al., *Bull. Chem. Soc. Jpn.*, 51 (8), 2401 (1978), a solution of 1-N-(2-iodoethyl)-2,3-dihydro-1H-imidazo[1,2-a]benzimidazole (2.20 g, 7.03 mmol), acetic acid (0.060 mL, 10.54 mmol) and DBU (1.57 mL, 10.54 mmol) in toluene (70 mL) was heated under reflux for 4 hours, cooled, and stirred at room temperature overnight. EtOAc (30 mL) was added and the mixture was washed with brine, dried (MgSO$_4$), and concentrated to give 1.68 g (98%) of a brown solid. This material was used without further purification in the next step (hydrolysis).

NMR (DMSO-d$_6$, 300 MHz): δ2.00 (s, 3H), 3.55 (t, J=5.4, 2H), 4.01 (m, 2H), 4.12 (m, 2H), 4.28 (t, J=5.4, 2H), 6.93 (m, 2H), 7.12 (m, 1H), 7.20 (dd, J=7.5, 1.8, 1H).

Step 5) Preparation of 1-N-(2-Hydroxyethyl)-2,3-dihydro-1H-imidazo[1,2-a]benzimidazole A solution of [2-(2,3-dihydro-1H-imidazo-[1,2-a]benzimidazol-1-yl)ethyl]acetate (1.67 g, 6.81 mmol) in 1N NaOH (13.6 mL) and dioxane (10 mL) was stirred at room temperature for 1 hour, concentrated, suspended in H$_2$O, and filtered to give 1.03 g of a brown solid.

Trituration with hot toluene (10 mL) gave 882 mg (64%) of an off-white solid m.p. 158°-160° C.

NMR (DMSO-d$_6$, 300 MHz): δ3.35 (t, J=5.7, 2H), 3.67 (t, J=5.7, 2H), 3.99 (m, 2H), 4.10 (m, 2H), 4.95 (brs, 1H), 6.92 (m, 2H), 7.11 (dd, J=6.7, 1.3, 1H), 7.17 (dd, J=7.9, 2.0, 1H).

Step 6) Preparation of 1-N-[2-(Methylamino)ethyl]-2,3-dihydro-1H-imidazo[1,2-a]benzimidazole To a cooled (0° C.), stirred suspension of 1-N-(2-hydroxyethyl)-2,3-dihydro-1H-imidazo[1,2-a]benzimidazole (882 mg, 4.34 mmol) in CH$_2$Cl$_2$ (18 mL) was added Et$_3$N (0.67 mL, 4.77 mmol) and MsCl (0.37 mL, 4.77 mmol). The resulting solution was stirred at room temperature for 1 hour, washed with brine, dried (MgSO$_4$) and concentrated to give an off-white solid. 33% CH$_3$NH$_2$/EtOH (45 mL) was added and the solution was stirred at room temperature over the weekend. The mixture was concentrated, taken up in 10% aqueous HOAc (20 mL) and extracted with EtOAc. The extracts were dried (MgSO$_4$) and concentrated to give 738 mg (79%) of an off-white solid m.p. 60°-63° C.

NMR (DMSO-d$_6$, 300 MHz): δ2.31 (s, 3H), 2.75 (t, J=6.4, 2H), 3.36 (t, J=6.4, 2H), 3.94 (m, 2H), 4.10 (m, 2H), 6.91 (m, 2H), 7.10 (dd, J=6.9, 1.5, 1H), 7.17 (dd, J=7.9, 2.1, 1H).

Step 7) Preparation of N-Methyl-N-[2-(2,3-dihydro-1H-imidazo[1,2-a]benzimidazol-1-yl)ethyl]-4-[(methylsulfonyl)amino]benzenesulfonamide Hydrochloride To a solution of 1-N-[2-(methylamino)ethyl]-2,3-dihydro-1H-imidazo[1,2-a]benzimidazole (725 mg, 3.35 mmol) and Et$_3$N (339 mg, 3.35 mmol) in CH$_2$Cl$_2$ (50 mL) was added 4-[(methylsulfonyl)amino]benzenesulfonyl chloride (904 mg, 3.35 mmol). After 45 minutes, the solution was washed with brine, saturated aqueous NaHCO$_3$, dried (MgSO$_4$), and concentrated to 20 mL. The precipitate was collected by filtration to give 1.35 g of product m.p. 205°-207° C. Saturated methanolic HCl (10 mL) was added to a suspension of free base in MeOH (5 mL). The solution was concentrated to about 10 mL and left standing. The resulting white crystals were collected by filtration to give 1.31 g (80%) of product m.p. 215°-217° C.

NMR (DMSO-d$_6$, 400 MHz): δ2.79 (s, 3H), 3.12 (s, 3H), 3.27 (t, J=5.1, 2H), 3.77 (t, J=5.1, 2H) 4.35 (m, 4H), 7.26 (m, 2H), 7.35 (d, J=8.9, 2H), 7.41 (m, 2H), 7.73 (d, J=8.9, 2H), 10.50 (s, 1H)

IR (KBr, cm$^{-1}$): 3400 (NH), 1675 (C=N)

MS (m/e): 450 (MH+)

Anal. Calcd. for C$_{19}$H$_{24}$ClN$_5$O$_4$S$_2$: C, 46.96; H, 4.98; N, 14.41%. Found: C, 46.56; H, 4.91; N, 14.19%.

EXAMPLE 19

N-Methyl-N-[2-[methyl(quinolin-2-yl)amino]ethyl-4-[methylsulfonyl)amino]benzamide A mixture of 2-[N-methyl-N-[(2-methylamino)ethyl]amino]quinoline (3.00 g, 13.93 mmol), 1-hydroxybenztriazole hydrate (1.88 g, 13.93 mmol), dicyclohexylcarbodiimide (2.88 g, 13.93 mmol), 4-[(methylsulfonyl)amino]benzoic acid (3.00 g, 13.93 mmol), and THF (45 mL) was stirred at room temperature for 20 hours. The precipitate was removed by filtration and the filtrate was concentrated. The remaining material was taken up in CHCl$_3$, and washed with saturated aqueous NaHCO$_3$ and brine, dried, and concentrated. Purification by flash chromatography gave 2.1 g of a white foam. The HCl salt was made, but could not be crystallized, and was reconverted to the free base. Recrystallization from iPrOH/EtOH and then EtOAc/EtOH gave 1.22 g (21%) of a white solid m.p. 154°-156° C.

Note: The compound exists as a mixture of amide rotamers. The chemical shifts for both rotamers are listed.

NMR (DMSO-d$_6$, 400 MHz): δ2.84 and 2.94 (brs, 3H), 2.91 and 2.97 (brs, 3H), 3.06 and 3.17 (brs, 3H), 3.50 and 3.69 (brs, 2H), 3.78 and 3.94 (brs, 2H), 7.02 (m, 4H), 7.16 (m, 2H), 7.48 (m, 2H), 7.66 (m, 1H), 7.95 (m, 1H), 9.88 (s, 1H).

IR (KBr, cm$^{-1}$): 1600 (C=O)

MS (m/e): 413 (MH+)

Anal. Calcd. for C$_{21}$H$_{24}$N$_4$O$_3$S: C, 61.15; H, 5.86; N, 13.58%. Found: C, 60.92; H, 5.98; N, 13.58%.

We claim:

1. The compounds of formula (I):

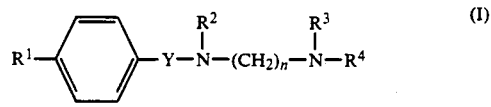

wherein R$^1$ is H, NHSO$_2$CH$_3$ or 1-imidazolyl; Y is SO$_2$ or C(O); n is 2 or 3; R$^2$ and R$^3$ are lower alkyl, containing 1 to 6 carbon atoms and R$^4$ is selected from the group consisting of:

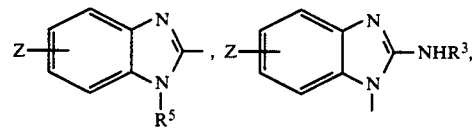

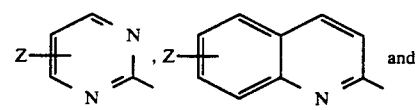

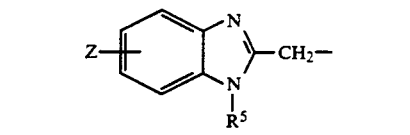

wherein R$^3$ and R$^5$ are lower alkyl containing 1 to 6 carbon atoms and Z is H or NHSO$_2$CH$_3$; or R$^3$ and R$^4$ are joined to form

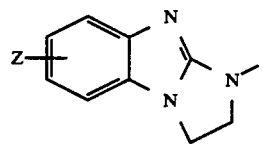

wherein Z is H or NHSO$_2$CH$_3$ or the pharmaceutically acceptable salt thereof.

2. The compounds according to claim 1 wherein R$^1$ is H or NHSO$_2$CH$_3$; Y is SO$_2$ or C(O); n is 2 or 3; R$^2$ and R$^3$ are lower alkyl containing 1 to 6 carbon atoms and R$^4$ is selected from the group consisting of:

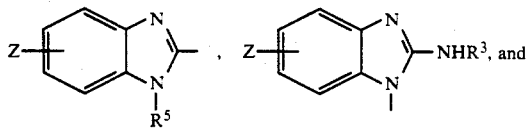
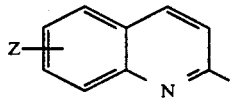

wherein R³ and R⁵ are lower alkyl containing 1 to 6 carbon atoms and Z is H or NHSO₂CH₃; or R³ and R⁴ are joined to form

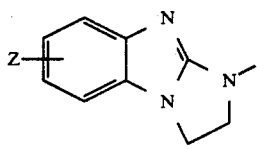

wherein Z is H or NHSO₂CH₃ or the pharmaceutically acceptable salt thereof.

3. The compound according to claim 2 N-methyl-N-[2-[methyl(1-methyl-1H-benzimidazol-2-yl)amino]ethyl-4-[(methylsulfonyl)amino]benzenesulfonamide and the pharmaceutically acceptable salts thereof.

4. The compound according to claim 1 4-[(methylsulfonyl)amino]-N-[2-(2-pyrimidinylamino)ethyl]benzenesulfonamide and the pharmaceutically acceptable salts thereof.

5. The compound according to claim 2 N-methyl-N-[2-[methyl(1-methyl-1H-benzimdazol-2-yl)amino]ethyl]-4-[(methylsulfonyl)amino]benzamide and the pharmaceutically acceptable salts thereof.

6. The compound according to claim 2 4-[(methylsulfonyl)amino]-N-[2-[(quinolin-2-yl)amino]ethyl]benzenesulfonamide and the pharmaceutically acceptable salts thereof.

7. The compound according to claim 2 N-methyl-N-[2-[methyl(1-ethyl-1-H-benzimidazol-2-yl)amino]ethyl]-4-[(methylsulfonyl)amino]benzenesulfonamide and the pharmaceutically acceptable salts thereof.

8. The compound according to claim 1 N-methyl-N-[2-[methyl[(1-methyl-1H-benzimidazol-2-yl)methyl]amino]ethyl]-4-[(methylsulfonyl)amino]benzamide and the pharmaceutically acceptable salts thereof.

9. The compound according to claim 1 N-methyl-N-[2-[methyl[(1-methyl-1H-benzimidazol-2-yl)methyl]amino]ethyl]-4-[(methylsulfonyl)amino]benzenesulfonamide and the pharmaceutically acceptable salts thereof.

10. The compound according to claim 2 N-methyl-N-[2-[methyl(quinolin-2-yl)amino]ethyl]-4-[](methylsulfonyl)amino]benzenesulfonamide and the pharmaceutically acceptable salts thereof.

11. The compound according to claim 2 N-methyl-N-[2-[methyl[5-[(methylsulfonyl)amino]-1H-benzimidazol-2-yl]amino]ethyl]benzamide and the pharmaceutically acceptable salts thereof.

12. The compound according to claim 2 N-methyl-N-[2-(2,3-dihydro-1H-imidazol[1,2-a]benzimidazol-1-yl)ethyl]-4-[(methylsulfonyl)amino]benzenesulfonamide and the pharmaceutically acceptable salts thereof.

13. The compound according to claim 2 N-methyl-N-[2-[methyl(quinolin-2-yl)amino]ethyl]-4-[(methylsulfonyl)amino]benzamide and the pharmaceutically acceptable salts thereof.

14. The compound according to claim 1 N-[2-[(1H-benzimidazol-2-ylmethyl)methylamino]ethyl]-N-methyl-4-[(methylsulfonyl)amino]benzenesulfonamide and the pharmaceutically acceptable salts thereof.

15. The compound according to claim 2 N-methyl-N-[3-[methyl(1-methyl-1H-benzimidazol-2-yl)amino]propyl]-4-[(methylsulfonyl)amino]benzenesulfonamide and the pharmaceutically acceptable salts thereof.

16. The compound according to claim 2 N-methyl-N-[2-[methyl(1H-benzimidazol-2-yl)amino]ethyl]-4-[(methylsulfonyl)amino]benzenesulfonamide and the pharmaceutically acceptable salts thereof.

17. The compound according to claim 2 N-methyl-N-[2-(2-methylamino)-1H-benzimidazol-1-yl)ethyl[-4-[(methylsulfonyl)amino]benzenesulfonamide and the pharmaceutically acceptable salts thereof.

18. The compound according to claim 2 N-[2-[(1-methyl-1H-benzimidazol-2-yl)amino]ethyl]-4-[(methylsulfonyl)amino]benzenesulfonamide and the pharmaceutically acceptable salts thereof.

19. The compound according to claim 2 N-methyl-N-[2-[(1-methyl-1H-benzimidazol-2-yl)amino]ethyl]-4-[(methylsulfonyl)amino]benzenesulfonamide and the pharmaceutically acceptable salts thereof.

20. A pharmaceutical composition having antiarrhythmic properties which comprises an effective amount of a compound of the formula (I) of claim 1 or its physiologically tolerated acid addition salt and a pharmaceutically acceptable carrier and/or diluent.

21. A method of treating arrhythmia which comprises administering an effective amount of a compound of the formula (I) of claim 1 or its pharmaceutically acceptable acid addition salt.

* * * * *